US012637418B2

(12) United States Patent
Oguro et al.

(10) Patent No.: US 12,637,418 B2
(45) Date of Patent: May 26, 2026

(54) HETEROCYCLIC COMPOUNDS AS ANTAGONIST OF NMDA

(71) Applicant: TAKEDA PHARMACEUTICAL COMPANY LIMITED, Osaka (JP)

(72) Inventors: Yuya Oguro, Kanagawa (JP); Makoto Kamata, Kanagawa (JP); Satoshi Mikami, Kanagawa (JP); Shinji Morimoto, Kanagawa (JP); Sachie Takashima, Kanagawa (JP); Masaki Daini, Kanagawa (JP); Osamu Kubo, Kanagawa (JP); Fumiaki Kikuchi, Kanagawa (JP); Akinori Toita, Kanagawa (JP); Florian Puenner, Kanagawa (JP); Takahito Kasahara, Kanagawa (JP); Masataka Murakami, Kanagawa (JP); Shuhei Ikeda, Kanagawa (JP); Fumie Yamaguchi, Kanagawa (JP); Minoru Nakamura, Kanagawa (JP); Takafumi Yukawa, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 910 days.

(21) Appl. No.: 17/310,164

(22) PCT Filed: Jan. 23, 2020

(86) PCT No.: PCT/JP2020/002216

§ 371 (c)(1),
(2) Date: Jul. 22, 2021

(87) PCT Pub. No.: WO2020/153414

PCT Pub. Date: Jul. 30, 2020

(65) Prior Publication Data

US 2022/0089525 A1 Mar. 24, 2022

(30) Foreign Application Priority Data

Jan. 24, 2019 (JP) ................................ 2019-010536

(51) Int. Cl.

| | |
|---|---|
| ***C07C 255/60*** | (2006.01) |
| ***A61P 25/06*** | (2006.01) |
| ***A61P 25/24*** | (2006.01) |
| ***A61P 25/28*** | (2006.01) |
| ***A61P 29/00*** | (2006.01) |
| ***C07D 213/82*** | (2006.01) |
| ***C07D 401/12*** | (2006.01) |
| ***C07D 409/12*** | (2006.01) |

(52) U.S. Cl.

CPC ............ *C07C 255/60* (2013.01); *A61P 25/06* (2018.01); *A61P 25/24* (2018.01); *A61P 25/28* (2018.01); *A61P 29/00* (2018.01); *C07D 213/82* (2013.01); *C07D 401/12* (2013.01); *C07D 409/12* (2013.01)

(58) Field of Classification Search

CPC ........ C07C 255/60; A61P 25/06; A61P 25/24; A61P 25/28; A61P 29/00; C07D 213/82; C07D 401/12; C07D 409/12

See application file for complete search history.

(56) References Cited

U.S. PATENT DOCUMENTS

| | | | |
|---|---|---|---|
| 4,382,938 | A | 5/1983 | Kaplan et al. |
| 5,252,563 | A | 10/1993 | Cordi et al. |
| 5,672,469 | A | 9/1997 | Hioki et al. |
| 5,840,732 | A | 11/1998 | Takatani et al. |
| 6,331,640 | B1 | 12/2001 | Fotouhi et al. |
| 6,387,938 | B1 | 5/2002 | Mizuguchi et al. |

(Continued)

FOREIGN PATENT DOCUMENTS

| | | | |
|---|---|---|---|
| AU | 2019204448 | B2 | 7/2019 |
| AU | 2021225156 | B2 | 9/2021 |

(Continued)

OTHER PUBLICATIONS

Taylor SJ, Soleymanzadeh F, Eldrup AB, Farrow NA, Muegge I, Kukulka A, Kabcenell AK, De Lombaert S. Design and synthesis of substituted nicotinamides as inhibitors of soluble epoxide hydrolase. Bioorg Med Chem Lett. Oct. 15, 2009;19(20):5864-8 (Year: 2009).*

(Continued)

*Primary Examiner* — Clinton A Brooks
*Assistant Examiner* — Izabela Schmidt
(74) *Attorney, Agent, or Firm* — Finnegan, Henderson, Farabow, Garrett & Dunner LLP

(57) ABSTRACT

A heterocyclic compound that can have an antagonistic action on an NMDA receptor containing the NR2B subunit, and is expected to be useful as a prophylactic or therapeutic agent for depression, bipolar disorder, migraine, pain, peripheral symptoms of dementia and the like is provided. A compound represented by the formula (I):

(I)

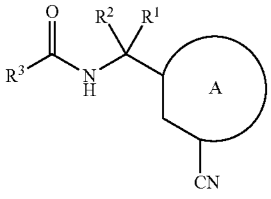

wherein each symbol is as described in the DESCRIPTION, or a salt thereof.

16 Claims, No Drawings

(56) References Cited

U.S. PATENT DOCUMENTS

| | | | |
|---|---|---|---|
| 6,420,415 B1 | 7/2002 | Yamashita et al. | |
| 9,469,601 B2 | 10/2016 | Vacher et al. | |
| 10,202,376 B2 | 2/2019 | Kimura et al. | |
| 10,807,987 B2 | 10/2020 | Oguro et al. | |
| 11,230,541 B2 | 1/2022 | Kimura et al. | |
| 11,471,428 B2 | 10/2022 | Hu et al. | |
| 11,702,419 B2 | 7/2023 | Oguro et al. | |
| 11,713,311 B2 | 8/2023 | Kimura et al. | |
| 11,827,601 B2 | 11/2023 | Ikeda et al. | |
| 11,834,409 B2 | 12/2023 | Ikeda et al. | |
| 11,952,344 B2 | 4/2024 | Oguro et al. | |
| 2002/0052512 A1 | 5/2002 | Fotouhi et al. | |
| 2002/0151534 A1 | 10/2002 | Ries et al. | |
| 2003/0119811 A1 | 6/2003 | Liverton et al. | |
| 2004/0006236 A1 | 1/2004 | Fotouhi et al. | |
| 2004/0147568 A1 | 7/2004 | Yu et al. | |
| 2004/0204409 A1 | 10/2004 | Ando et al. | |
| 2005/0080119 A1 | 4/2005 | Fotouhi et al. | |
| 2005/0137187 A1 | 6/2005 | Souers et al. | |
| 2005/0165064 A1 | 7/2005 | Kajino et al. | |
| 2007/0155671 A1 | 7/2007 | Fotouhi et al. | |
| 2008/0234318 A1 | 9/2008 | Gudmundsson et al. | |
| 2009/0048303 A1 | 2/2009 | Borza et al. | |
| 2009/0099184 A1* | 4/2009 | Delombaert ......... | C07D 213/81 546/261 |
| 2010/0331335 A1 | 12/2010 | Sham et al. | |
| 2012/0238569 A1 | 9/2012 | Gillespie et al. | |
| 2012/0258950 A1 | 10/2012 | Andrews et al. | |
| 2013/0072494 A1 | 3/2013 | Sham et al. | |
| 2014/0315945 A1 | 10/2014 | Campbell et al. | |
| 2016/0031907 A1 | 2/2016 | Campbell et al. | |
| 2016/0244464 A1 | 8/2016 | Campbell et al. | |
| 2017/0334896 A1 | 11/2017 | Liu et al. | |
| 2017/0362223 A1 | 12/2017 | Kimura et al. | |
| 2019/0300536 A1 | 10/2019 | Oguro et al. | |
| 2020/0231579 A1 | 7/2020 | Kimura et al. | |
| 2021/0332053 A1 | 10/2021 | Oguro et al. | |
| 2022/0089525 A1 | 3/2022 | Oguro et al. | |
| 2022/0388995 A1 | 12/2022 | Kimura et al. | |
| 2023/0002318 A1 | 1/2023 | Ikeda et al. | |
| 2023/0134307 A1 | 5/2023 | Ikeda et al. | |
| 2023/0150934 A1 | 5/2023 | Ikeda et al. | |

FOREIGN PATENT DOCUMENTS

| | | | |
|---|---|---|---|
| CA | 2439231 A1 | 9/2002 |
| EP | 1 500 658 A1 | 1/2005 |
| EP | 3 239 150 A1 | 11/2017 |
| EP | 3 342 772 A1 | 7/2018 |
| JP | 5798283 A | 6/1982 |
| JP | 8137043 A | 5/1996 |
| JP | 8319288 A | 12/1996 |
| JP | H11-514333 T | 12/1999 |
| JP | 2000/159747 A | 6/2000 |
| JP | 2001-500852 T | 1/2001 |
| JP | 2003/512422 A | 4/2003 |
| JP | 2004/002405 A | 1/2004 |
| JP | 2004161716 A | 6/2004 |
| JP | 2005511478 A | 4/2005 |
| JP | 2006-502162 A | 1/2006 |
| JP | 2006522794 A | 10/2006 |
| JP | 2008508248 A | 3/2008 |
| JP | 2009-528992 A | 8/2009 |
| JP | 2012517439 A | 8/2012 |
| JP | 2013522171 A | 6/2013 |
| JP | 2014-510131 A | 4/2014 |
| JP | 2016502555 A | 1/2016 |
| WO | WO 1996/028471 A1 | 9/1996 |
| WO | WO 98/01429 A1 | 1/1998 |
| WO | WO 1998/008868 A1 | 3/1998 |
| WO | WO 00/21920 A1 | 4/2000 |
| WO | WO 2001/000663 A2 | 1/2001 |
| WO | WO 01/30330 A2 | 5/2001 |
| WO | WO 01/32174 A1 | 5/2001 |
| WO | WO 02/072558 A1 | 9/2002 |
| WO | WO 02/080928 A1 | 10/2002 |
| WO | WO 03/035641 A1 | 5/2003 |
| WO | WO 2004/021984 | 3/2004 |
| WO | WO 2014/086825 A1 | 6/2004 |
| WO | WO 2004089366 A1 | 10/2004 |
| WO | WO 2007/021308 A1 | 2/2007 |
| WO | WO 2007/027999 A2 | 3/2007 |
| WO | WO 2007/075387 A1 | 7/2007 |
| WO | WO 2007/078523 A2 | 7/2007 |
| WO | WO 2007/098352 A2 | 8/2007 |
| WO | WO 2009/004430 A1 | 1/2009 |
| WO | WO 2010/091310 A1 | 8/2010 |
| WO | WO 2011/109441 A1 | 9/2011 |
| WO | WO 2012/123471 A1 | 9/2012 |
| WO | WO 2012/137089 A1 | 10/2012 |
| WO | WO 2012/174199 A1 | 12/2012 |
| WO | WO 2014/134388 A1 | 9/2014 |
| WO | WO 2014/172044 A1 | 10/2014 |
| WO | WO 2015/127391 A1 | 2/2015 |
| WO | WO 2016/104434 A1 | 6/2016 |
| WO | WO 2017/027343 | 2/2017 |
| WO | WO 2017/027345 | 2/2017 |
| WO | WO 2017/174158 | 10/2017 |
| WO | WO 2019/022179 A1 | 1/2019 |
| WO | WO 2019/189945 A1 | 10/2019 |
| WO | WO 2020/081999 A1 | 4/2020 |
| WO | WO 2020/153414 A1 | 7/2020 |
| WO | WO 2020/154314 | 7/2020 |
| WO | WO 2020/196828 A1 | 10/2020 |
| WO | WO 2020/198710 A1 | 10/2020 |
| WO | WO 2021/094832 A1 | 5/2021 |

OTHER PUBLICATIONS

Taylor et al., Bioorg Med Chem Lett. Oct. 15, 2009;19(20):5864-8. (Year: 2009).*

Borza et al., "Benzimidazole-2-carboxamides as novel NR2B selective NMDA receptor antagonists," Bioorganic & Medicinal Chemistry Letters, 2006, 16:4638-4640.

Caddy et al., "Ketamine as the prototype glutamatergic antidepressant: pharmacodynamic actions, and a systematic review and meta-analysis of efficacy," Ther. Adv. Psychopharmacol., 2014, 4:75-99.

Davies et al., "A novel series of benzimidazole NR28-selective NMDA receptor antagonists," Bioorg. Med. Chem. Lett, 2012, 22:2620-2623.

Devonshire et al., "Effects of urethane anaesthesia on sensory processing in the rat barrel cortex revealed by combined optical imaging and electrophysiology," Eur. J. Neurosci., 2010, 32:786-797.

Howlett et al., ""Inhibition of fibril formation in b-amyloid peptide by a novel series of benzofurans,"" Biochem. J. 1999, 340 (1) :283-289.

Ladarola et al., "Ketamine and other N-methyl-D-aspartate receptor antagonists in the treatment of depression: a perspective review," Ther. Adv. Chronic. Dis. 2015, 6(3): 97-114.

Jin et al., "Developmental Expression, Subcellular Localization, and Tyrosine Phosphorylation of NR2A and NR28 in the Rat Brain," Mal. Cells, 1997, 7(1):64-71.

Jonas et al. "Differences in Ca2• permeability of AMPA-type glutamate receptor channels in neocortical neurons caU.S.ed by differential GluR-B subunit expression," Neuron, 1994, 12: 1281-1289.

Kandiah et al., "Cerebral white matter disease is independently associated with BPSD in Alzheimer's disease," J. Neural. Sci. 2014, 337: 162-166.

Kim et al., "Effect of NMDA NR2B antagonist on neuropathic pain in two spinal cord injury models," Pain, 2012, 153: 1022-1029.

Maidment et al., "Efficacy of Memantine on Behavioral and Psychological Symptoms Related to Dementia: A Systematic Meta-Analysis," Ann. Pharmacother., 2008, 42: 32-38.

Matsumura et al, "Impairment of CaMKII activation and attenuation of neuropathic pain in mice lacking NR2B phosphorylated at Tyr1471", Eur. J. Neurosci. 2010, 32: 798-810.

(56) References Cited

OTHER PUBLICATIONS

Monyer et al., "Developmental and Regional Expression in the Rat Brain and Functional Properties of Four NMDA Receptors," Neuron, Mar. 1994, 12:529-540.
Peeters, M. et al., Effects of Pan- and Subtype-Selective N-Methyl-D-aspartate Receptor Antagonists on Cortical Spreading Depression in the Rat: Therapeutic Potential for Migraine, The Journal of Pharmacology and Experimental Therapeutics (J. Pharmacol. Exp. Ther.) vol. 321, p. 564-572, 2007.
Preskorn, S. H. et al., An Innovative Design to Establish Proof of Concept of the Antidepressant Effects of the NR2B Subunit Selective N-Methyl-D-Aspartate Antagonist, CP-101,606, in Patients With Treatment-Refractory Major Depressive Disorder, Journal of Clinical Psychopharmacology (J. Clin. Psychopharmacol.) vol. 28, p. 631-637, 2008.
Shityakov et al,. "a-Cyclodextrin dimer complexes of dopamine and levodopa derivatives to assess drug delivery to the central nervoU.S. system: ADME and molecular docking studies," International Journal of Nanomedicine, 2012, 7:3211-3219.
STN Registry Entry for "Benzeneacetamide, 2-chloro-N-(pyrazolo [1,5-a] pyrimidin-3-ylmethyl)-" (1638470-82-2) (one page).
Thompson et al., Accession No. 2018:2481709, Document No. 170: 112996, entered STN, Dec. 13, 2018 (3 pages).
Watanabe et al., "Distinct Distributions of Five N-Methyl-D-Aspartate Receptor Channel Subunit mRNAs in the Forebrain," The Journal of Comparative Neurology, 1993, 338:377-390.
Wu et al., "Targeting the NMDA Receptor Subunit NR2B for the Treatment of Neuropathic Pain," Neurotherapeutics, 2009, 6, 4:693-702.
Lally, "Ivabradine, a novel treatment for clozapine-induced sinus tachycardia: a case series", Therapeutic Advances in Psychopharmacology (Ther. Adv. Psychopharmacol.), vol. 4, pp. 117-122, 2014.
U.S. Appl. No. 17/010,666, filed Sep. 2, 2020 by Oguro et al.
Brown, Dean G. et al., "2,6-Disubstituted pyrazines and related analogs as NR2B site antagonists of the NMDA receptor with anti-depressant activity," Bioorganic & Medicinal Chemistry Letters, Elsevier Amsterdam NL, vol. 21, No. 11, Mar. 31, 2011, pp. 3399-3403.
Database Registry [Online] Chemical Abstracts Service, Columbus, Ohio, US; Dec. 8, 2013, Aurora Fine Chemicals C: "-2-Thiophenecarboxamide, N-[(N-cyano-2-fluorophenyl)methyl]-4-methoxy-", XP055959594, Database accession No. 1510812-10-8, abstract.
Database Registry [Online] Chemical Abstracts Service, Columbus, Ohio, US; Dec. 8, 2013, Aurora Fine Chemicals C: "-2-Thiophenecarboxamide, N-[(N-cyano-2-fluorophenyl)methyl]-4-methoxy-", XP055959595, Database accession No. 1489651-31-1, abstract.
Kawai et al., "Structure-activity relationship study of novel NR2B-selective antagonists with arylamides to avoid reactive metabolites formation", Bioorganic & Medicinal Chemistry Letters, Elsevier, Amsterdam NL, vol. 17, No. 20, Sep. 14, 2007, pp. 5537-5542.
English Translation of International Search Report for PCT/JP2020/002216 dated Apr. 14, 2020 (3 pages).
Registry (STN) for CAS registration No. 1349423-75-1, 3-Pyridinecarboxamide, N-[2-chloro-4-cyanophenyl)methyl]-6-(3,3,3-trifluoropropoxy)-(CA Index Name) (entered Dec. 6, 2011) and CAS registration No. 1406153-87-4, Benzamide, N-[(4-cyano-2-fluorophenyl)methyl]-4-methoxy-(CA Index Name) (entered Nov. 25, 2012) (6 pages).
Taylor, Steven J. et al., "Design and Synthesis of Substituted Nicotinamides as Inhibitors of Soluble Epoxide Hydrolase," Bioorganic and Medicinal Chemistry Letters, 2009, 19, 5864-5868.
Egunlusi, A. O., et al., "NMDA Receptor Antagonists: Emerging Insights into Molecular Mechanisms and Clinical Applications in Neurological Disorders," *Pharmaceuticals* (Basel), 17, 639 (2024) (27 pages).
Meng-Lin L, et al., "LY395756, an mGluR2 agonist and mGluR3 antagonist, enhances NMDA receptor expression and function in the normal adult rat prefrontal cortex, but fails to improve working memory and reverse MK801-induced working memory impairment," *Experimental Neurology*, vol. 273, pp. 190-201 (2015).
Moore, T. J., et al., "Safety and effectiveness of NMDA receptor antagonists for depression: A multidisciplinary review," *Pharmacotherapy*, 42, pp. 567-579 (2022).
Parikh, B., et al., "Preventive analgesia: Effect of small dose of ketamine on morphine requirement after renal surgery," *Journal of Anaesthesiology Clinical Pharmacology*, vol. 27, Issue 4, pp. 485-488 (2011).
Sperling, R. A., et al., "Toward defining the preclinical stages of Alzheimer's disease: Recommendations from the National Institute on Aging-Alzheimer's Association workgroups on diagnostic guidelines for Alzheimer's disease," *Alzheimers Dement.*, 7(3), pp. 280-292 (2011).
Trang, T., et al., "Pain and Poppies: The Good, the Bad, and the Ugly of Opioid Analgesics," *The Journal of Neuroscience*, 35(41), pp. 13879-13888 (2015).
Gitto et al., "From NMDA Receptor Antagonists to Discovery of Selective 02 Receptor Ligands," Bioorganic & Medicinal Chemistry, 2014, vol. 22, No. 1, p. 393-397.

* cited by examiner

HETEROCYCLIC COMPOUNDS AS ANTAGONIST OF NMDA

TECHNICAL FIELD

The present invention relates to a heterocyclic compound that can have an antagonistic action on an N-methyl-D-aspartic acid (NMDA) receptor containing the NR2B subunit, and that is expected to be useful as a prophylactic or therapeutic agent for depression, bipolar disorder, migraine, pain, peripheral symptoms of dementia and the like.

BACKGROUND OF THE INVENTION

The major excitatory neurotransmitter in the central nervous system such as the brain, spinal cord and the like is glutamic acid, and its signal transduction is mediated by N-methyl-D-aspartic acid (NMDA) receptor, gamma-amino-3-hydroxy-5-methyloxazole-4-propionic acid (AMPA)/kainic acid (KA) receptor and metabotropic glutamate receptor. Among these, NMDA receptor is highly permeable to cations including calcium ion and mediates excitatory neurotransmission by depolarizing nerve cells. In addition, calcium flowing into the cell via NMDA receptor functions as a secondary messenger, and causes plastic changes in the nerve function through actions such as changes in the intracellular phosphorylation signal, regulation of transcription and translation of the gene, and the like. Thus, NMDA receptor plays an important role in the functional regulation of central nervous system.

The NMDA receptor is a receptor composed of a tetramer in which 2 or 3 subunits from among NR1, NR2A, NR2B, NR2C, NR2D, NR3A, NR3B subunits are associated, and essentially requires the presence of NR1 subunit in order to have the function of a receptor responsible for excitatory neurotransmission. Since the NR1 subunit is contained in all NMDA receptors having the function, it is widely distributed in the central nervous system; however, the distribution and the timing of expression of the NR2 subunit are different for each subunit. For example, NR2A and NR2C subunits are detected only immediately before birth, whereas NR2B and NR2D subunits are observed from an early stage in embryonic development. For example, while the NR2A subunit is widely distributed in the brain, the NR2B subunit is locally expressed in the forebrain, and the NR2C subunit is locally expressed in the cerebellum (non-patent document 1).

An NMDA receptor containing the NR2B subunit, which is the target in the present invention, is highly expressed in the cerebral cortex (particularly the second or third layer), hippocampus, amygdala, ventral nucleus of thalamus, and olfactory bulb in the brain of adult rodents. The NMDA receptor is confined to the dorsal horn of the spinal cord (particularly the second layer) in the spinal cord (non-patent document 2). Moreover, in a single cell, the NMDA receptor containing the NR2B subunit is most highly expressed in postsynaptic density and the expression is also found in the extrasynaptic region (non-patent document 3). This suggests that an NMDA receptor containing the NR2B subunit functions widely in the brain and is effective for the prophylaxis or treatment of central diseases.

Patent document 1 discloses the following compound having an antibacterial action and useful as a pesticide or the like.

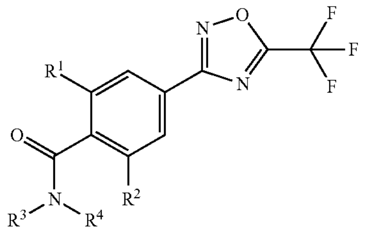

wherein each symbol is as defined in the document.

Patent document 2 discloses the following compound having a calcitonin gene-related peptide (CGPR) receptor antagonistic action, and useful for the prophylaxis, treatment, and the like of migraine, nerve system disease, and the like.

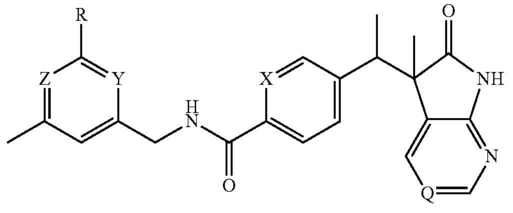

wherein each symbol is as defined in the document.

Patent document 3 discloses the following compound having a CGPR receptor antagonistic action, and useful for the prophylaxis, treatment, and the like of migraine, nerve system disease, and the like.

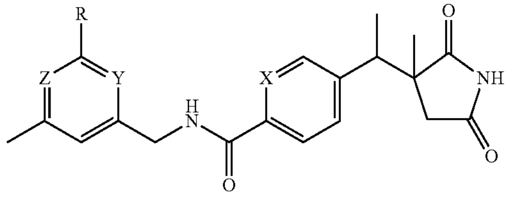

wherein each symbol is as defined in the document.

Patent document 4 discloses the following compound having a cell proliferation suppressive action, and useful for the prophylaxis, treatment, and the like of cancer (hematological cancer, etc.), and the like.

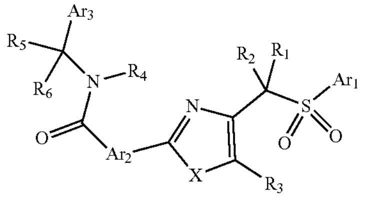

wherein each symbol is as defined in the document.

Patent document 5 discloses the following compound having an FXa inhibitory action, and useful for the suppression of blood coagulation, prophylaxis or treatment of thrombus and embolus, and the like.

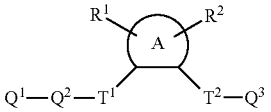

wherein each symbol is as defined in the document.

Patent document 6 discloses the following compound having an FXa inhibitory action and useful for antithrombosis, and the like.

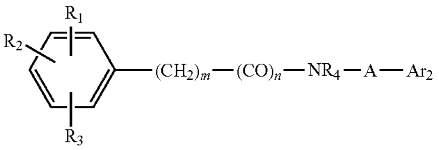

wherein each symbol is as defined in the document.

Patent document 7 discloses the following compound having a PPAR agonistic action, and useful for the improvement of insulin resistance, and prophylaxis, treatment, and the like of diabetes, X syndrome, gastrointestinal inflammatory diseases, and the like.

(I)

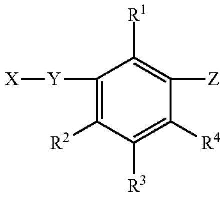

wherein each symbol is as defined in the document.

Patent document 8 discloses the following compound having a PPARγ agonistic action, and useful for the prophylaxis, treatment, and the like of digestive tract diseases (ulcerative colitis, Crohn's disease, pancreatitis, gastritis etc.) and the like.

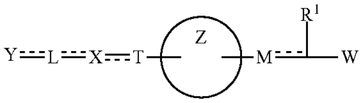

wherein each symbol is as defined in the document.

Patent document 9 discloses the following compound having an FXa inhibitory action, and useful for antithrombosis, and the like.

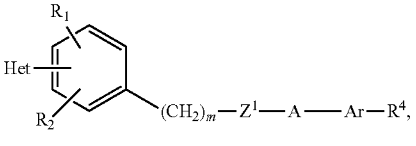

wherein each symbol is as defined in the document.

Patent document 10 discloses the following compound having a PPAR inhibitory action, and useful for the improvement of insulin resistance, and prophylaxis, treatment, and the like of diabetes, X syndrome, and the like.

(I)

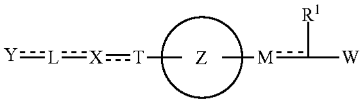

wherein each symbol is as defined in the document.

Patent document 11 discloses the following compound having an enhancer of zeste homolog (EZH) inhibitory action, and useful for the prophylaxis, treatment, and the like of cancer (including CNS), and the like.

(I)

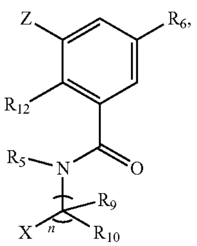

wherein each symbol is as defined in the document.

Patent document 12 discloses the following compound having an NR2B subunit-containing NMDA receptor-specific negative allosteric modulator action, and useful for the prophylaxis, treatment, and the like of depression, bipolar disorder, migraine, pain, peripheral symptoms of dementia, and the like.

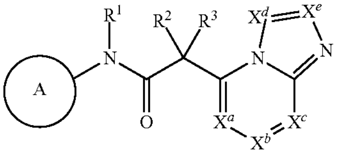

wherein each symbol is as defined in the document.

DOCUMENT LIST

Patent Documents patent document 1: WO 2017/174158
patent document 2: WO 2017/027343
patent document 3: WO 2017/027345
patent document 4: WO 2012/158691
patent document 5: WO 2008/111299
patent document 6: US 2002/0151534
patent document 7: WO 02/081428
patent document 8: WO 02/080899
patent document 9: WO 02/072558
patent document 10: WO 01/025181
patent document 11: WO 2014/172044
patent document 12: WO 2016/104434

Non-Patent Documents non-patent document 1: Neuron, vol. 12, pages 529-540, 1994
non-patent document 2: J. Comp. Neurol., vol. 338, pages 377-390, 1993
non-patent document 3: Mol. Cells, vol. 7, pages 64-71, 1997

SUMMARY OF INVENTION

Technical Problem

The present invention aims to provide a heterocyclic compound that may have an antagonistic action on NMDA receptor containing the NR2B subunit, and that is expected to be useful as a prophylactic or therapeutic agent for depression, bipolar disorder, migraine, pain, peripheral symptoms of dementia, and the like, and a medicament containing the same.

Solution to Problem

The present inventors have conducted intensive studies in an attempt to solve the above-mentioned problems, and found that a compound represented by the following formula (I) may have a superior antagonistic action on an NMDA receptor containing the NR2B subunit, which resulted in the completion of the present invention.

That is, the present invention provides the following.

[1] A compound represented by the formula (I):

(I)

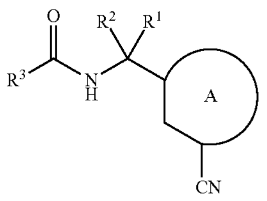

wherein ring A is a 6-membered aromatic ring further substituted by 1 to 4 substituents selected from (1) a $C_{1-3}$ alkyl group, (2) a $C_{1-3}$ haloalkyl group, (3) an optionally substituted cyclic group, (4) an optionally substituted $C_{1-6}$ alkoxy group, and (5) a halogen atom;

$R^1$ and $R^2$ are each independently a hydrogen atom or a $C_{1-3}$ alkyl group optionally substituted by fluorine atom(s);

$R^3$ is (1) a group represented by

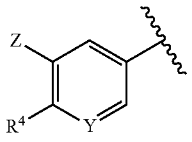

wherein $R^4$ is a substituent selected from (1) a $C_{1-3}$ haloalkyl group, (2) an optionally substituted $C_{3-7}$ cycloalkyl group, and (3) an optionally substituted $C_{1-6}$ alkoxy group, Y is a nitrogen atom or $CR^6$, $R^6$ is a hydrogen atom or a halogen atom, and Z is a hydrogen atom or a halogen atom, or (2) a group represented by

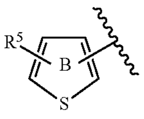

wherein $R^5$ is a substituent selected from (1) a $C_{1-3}$ haloalkyl group, (2) an optionally substituted $C_{3-7}$ cycloalkyl group, and (3) an optionally substituted $C_{1-6}$ alkoxy group, and ring B is a thiophene ring optionally further substituted by one halogen atom, or a salt thereof (sometimes to be abbreviated as "compound (I)" in the present specification).

[2] The compound of [1], wherein ring A is a 6-membered aromatic ring further substituted by 1 or 2 substituents selected from (1) a $C_{1-3}$ alkyl group, (2) a $C_{3-10}$ cycloalkyl group, (3) a $C_{1-6}$ alkoxy group optionally substituted by 1 to 3 halogen atoms, and (4) a halogen atom;

$R^1$ and $R^2$ are each a hydrogen atom;

$R^3$ is (1) a group represented by

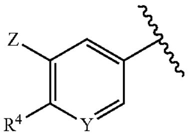

wherein $R^4$ is a $C_{1-3}$ haloalkyl group or a $C_{1-6}$ alkoxy group optionally substituted by 1 to 3 halogen atoms, Y is a nitrogen atom or $CR^6$, $R^6$ is a hydrogen atom, Z is a halogen atom or a hydrogen atom; or (2) a group represented by

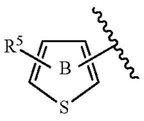

wherein $R^5$ is a $C_{1-3}$ haloalkyl group, and ring B is a thiophene ring optionally further substituted by one halogen atom;

or a salt thereof.

[3] N-[(5-cyano-2-methoxypyridin-3-yl)methyl]-6-(difluoromethoxy)-5-fluoropyridine-3-carboxamide or a salt thereof.

[4] N-[(3-cyano-2-fluoro-6-methoxyphenyl)methyl]-6-(difluoromethoxy)-5-fluoropyridine-3-carboxamide or a salt thereof.

[5] A medicament comprising the compound of [1] or a salt thereof.

[6] The medicament of [5], wherein the medicament is an antagonist of an NMDA receptor containing an NR2B subunit.

[7] The medicament of [5], wherein the medicament is a prophylactic or therapeutic agent for depression, bipolar disorder, migraine, pain, or peripheral symptoms of dementia.

[8] The compound of [1] or a salt thereof for use in the prophylaxis or treatment of depression, bipolar disorder, migraine, pain, or peripheral symptoms of dementia.

[9] A method for antagonizing an NMDA receptor containing an NR2B subunit in a mammal, comprising administering an effective amount of the compound of [1] or a salt thereof to the mammal.

[10] A method for preventing or treating depression, bipolar disorder, migraine, pain, or peripheral symptoms of dementia in a mammal, comprising administering an effective amount of the compound of [1] or a salt thereof to the mammal.

[11] Use of the compound of [1] or a salt thereof for the production of a prophylactic or therapeutic agent for depression, bipolar disorder, migraine, pain, or peripheral symptoms of dementia.

Advantageous Effects of Invention

The present invention provides a heterocyclic compound that may have an antagonistic action on an NMDA receptor containing the NR2B subunit and that is expected to be useful as a prophylactic or therapeutic agent for depression, bipolar disorder, migraine, pain, peripheral symptoms of dementia, and the like, and a medicament containing the same.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]

(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),

(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms elected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms elected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms elected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbocycle" include a $C_{6-14}$ aromatic hydrocarbocycle, $C_{3-10}$ cycloalkane and $C_{3-10}$ cycloalkene.

In the present specification, examples of the "$C_{6-14}$ aromatic hydrocarbocycle" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms elected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms elected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxathiine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms elected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, the "$C_{1-3}$ alkyl group" is, for example, the above-mentioned "$C_{1-6}$ alkyl group" having 1 to 3 carbon atoms.

In the present specification, the "$C_{1-3}$ haloalkyl group" is, for example, the above-mentioned "$C_{1-3}$ alkyl group" having 1 to 7, preferably 1 to 5, "halogen atoms" mentioned above.

In the present specification, the "$C_{3-7}$ cycloalkyl group" is, for example, the above-mentioned "$C_{3-10}$ cycloalkyl group" having 3 to 7 carbon atoms.

In the present specification, the "cyclic group" is, for example, the above-mentioned "$C_{3-10}$ cycloalkyl group", "$C_{3-10}$ cycloalkenyl group", "$C_{6-14}$ aryl group", or "heterocyclic group".

In the present specification, the "6-membered aromatic ring" is, for example, a benzene ring or a 6-membered "aromatic heterocycle" from those mentioned above.

The definition of each symbol in the formula (I) is explained below.

ring A is a 6-membered aromatic ring further substituted by 1 to 4 substituents selected from (1) a $C_{1-3}$ alkyl group,
(2) a $C_{1-3}$ haloalkyl group,
(3) an optionally substituted cyclic group,
(4) an optionally substituted $C_{1-6}$ alkoxy group, and
(5) a halogen atom.

As the "6-membered aromatic ring" for ring A, a benzene ring or a pyridine ring is preferable.

As the "cyclic group" of the "optionally substituted cyclic group" as the substituent of ring A, a $C_{3-10}$ cycloalkyl group (e.g., cyclopropyl) is preferable. As used herein, the "cyclic group" optionally has 1 to 3 substituents selected from the aforementioned substituent group A. As such "substituent", a halogen atom (e.g., fluorine atom) is preferable.

The "$C_{1-6}$ alkoxy group" of the "optionally substituted $C_{1-6}$ alkoxy group" as the substituent of ring A optionally has 1 to 3 substituents selected from the aforementioned substituent group A. As such "substituent", a halogen atom (e.g., fluorine atom) is preferable.

Ring A is preferably a 6-membered aromatic ring (e.g., benzene ring, pyridine ring) further substituted by 1 to 4 substituents selected from (1) a $C_{1-3}$ alkyl group (e.g., methyl),
(2) an optionally substituted cyclic group (e.g., $C_{3-10}$ cycloalkyl group (e.g., cyclopropyl)),
(3) an optionally substituted $C_{1-6}$ alkoxy group (e.g., methoxy, ethoxy), and
(4) a halogen atom (e.g., fluorine atom, bromine atom), more preferably, a 6-membered aromatic ring (e.g., benzene ring, pyridine ring) further substituted by 1 to 3 substituents selected from
(1) a $C_{1-3}$ alkyl group (e.g., methyl),
(2) a $C_{3-10}$ cycloalkyl group (e.g., cyclopropyl),
(3) a $C_{1-6}$ alkoxy group (e.g., methoxy, ethoxy) optionally substituted by 1 to 3 halogen atoms (e.g., fluorine atom), and
(4) a halogen atom (e.g., fluorine atom, bromine atom).

As used herein, at least one of the substituents of the 6-membered aromatic ring is preferably present at the para-position with respect to the cyano group on ring A.

$R^1$ and $R^2$ are each independently a hydrogen atom or a $C_{1-3}$ alkyl group optionally substituted by a fluorine atom.

$R^1$ and $R^2$ are each preferably a hydrogen atom.

$R^3$ is (1) a group represented by

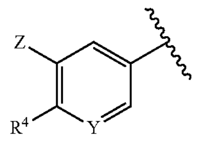

wherein $R^4$ is a substituent selected from
(1) a $C_{1-3}$ haloalkyl group,
(2) an optionally substituted $C_{3-7}$ cycloalkyl group, and
(3) an optionally substituted $C_{1-6}$ alkoxy group,
Y is a nitrogen atom or $CR^6$,
$R^6$ is a hydrogen atom or a halogen atom, and
Z is a hydrogen atom or a halogen atom, or
(2) a group represented by

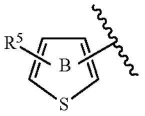

wherein $R^5$ is a substituent selected from (1) a $C_{1-3}$ haloalkyl group, (2) an optionally substituted $C_{3-7}$ cycloalkyl group, and (3) an optionally substituted $C_{1-6}$ alkoxy group, and ring B is a thiophene ring optionally further substituted by one halogen atom.

The "$C_{3-7}$ cycloalkyl group" of the "optionally substituted $C_{3-7}$ cycloalkyl group" for $R^4$ optionally has 1 to 3 substituents selected from the aforementioned substituent group A. As such "substituent", a halogen atom (e.g., fluorine atom) is preferable.

The "$C_{1-6}$ alkoxy group" of the "optionally substituted $C_{1-6}$ alkoxy group" for $R^4$ optionally has 1 to 3 substituents selected from the aforementioned substituent group A. As such "substituent", a halogen atom (e.g., fluorine atom) is preferable.

$R^4$ is preferably an optionally substituted $C_{1-6}$ alkoxy group (e.g., methoxy), more preferably, a $C_{1-6}$ alkoxy group (e.g., methoxy) optionally substituted by 1 to 3 halogen atoms (e.g., fluorine atom).

Other preferred embodiment of $R^4$ is a $C_{1-3}$ haloalkyl group (e.g., trifluoromethyl) or a $C_{1-6}$ alkoxy group (e.g., methoxy) optionally substituted by 1 to 3 halogen atoms (e.g., fluorine atom).

Y is preferably a nitrogen atom.

$R^6$ is preferably a hydrogen atom.

Z is preferably a halogen atom, further preferably a fluorine atom.

The "$C_{3-7}$ cycloalkyl group" of the "optionally substituted $C_{3-7}$ cycloalkyl group" for $R^5$ optionally has 1 to 3 substituents selected from the aforementioned substituent group A. As such "substituent", a halogen atom (e.g., fluorine atom) is preferable.

The "$C_{1-6}$ alkoxy group" of the "optionally substituted $C_{1-6}$ alkoxy group" for $R^5$ optionally has 1 to 3 substituents selected from the aforementioned substituent group A. As such "substituent", a halogen atom (e.g., fluorine atom) is preferable.

$R^5$ is preferably a $C_{1-3}$ haloalkyl group (e.g., difluoromethyl, trifluoromethyl).

ring B is preferably a thiophene ring further substituted by one halogen atom (e.g., fluorine atom).

$R^3$ is preferably a group represented by

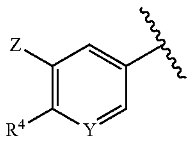

wherein $R^4$ is a $C_{1-3}$ haloalkyl group (e.g., trifluoromethyl) or an optionally substituted $C_{1-6}$ alkoxy group (e.g., methoxy), Y is a nitrogen atom or $CR^6$, $R^6$ is a hydrogen atom or a halogen atom (e.g., fluorine atom), Z is a hydrogen atom or a halogen atom (e.g., fluorine atom), more preferably, a group represented by

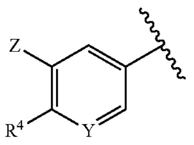

wherein $R^4$ is a $C_{1-6}$ alkoxy group (e.g., methoxy) optionally substituted by 1 to 3 halogen atoms (e.g., fluorine atom), Y is a nitrogen atom, and Z is a halogen atom (e.g., fluorine atom).

Another preferred embodiment of $R^3$ is a group represented by

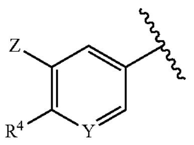

wherein $R^4$ is a $C_{1-3}$ haloalkyl group (e.g., trifluoromethyl) or a $C_{1-6}$ alkoxy group (e.g., methoxy) optionally substituted by 1 to 3 halogen atoms (e.g., fluorine atom), Y is $CR^6$, one of $R^6$ and Z is a halogen atom (e.g., fluorine atom), and the other is a hydrogen atom.

Preferred examples of compound (I) include the following compounds.

[Compound I-1]

Compound (I) wherein ring A is a 6-membered aromatic ring (e.g., benzene ring, pyridine ring) further substituted by 1 to 4 substituents selected from (1) a $C_{1-3}$ alkyl group (e.g., methyl), (2) an optionally substituted cyclic group (e.g., $C_{3-10}$ cycloalkyl group (e.g., cyclopropyl)), (3) an optionally substituted $C_{1-6}$ alkoxy group (e.g., methoxy, ethoxy), and (4) a halogen atom (e.g., fluorine atom, bromine atom);

$R^1$ and $R^2$ are each a hydrogen atom;

$R^3$ is (1) a group represented by

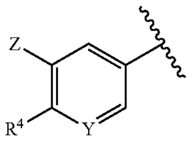

wherein $R^4$ is a $C_{1-3}$ haloalkyl group (e.g., trifluoromethyl) or an optionally substituted $C_{1-6}$ alkoxy group (e.g., methoxy), Y is a nitrogen atom or $CR^6$, $R^6$ is a hydrogen atom or a halogen atom (e.g., fluorine atom), and Z is a hydrogen atom or a halogen atom (e.g., fluorine atom); or (2) a group represented by

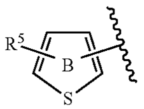

wherein $R^5$ is a $C_{1-3}$ haloalkyl group (e.g., difluoromethyl, trifluoromethyl), and ring B is a thiophene ring optionally further substituted by one halogen atom (e.g., fluorine).

[Compound I-2]

Compound (I) wherein ring A is a 6-membered aromatic ring (e.g., benzene ring, pyridine ring) further substituted by 1 or 2 substituents selected from (1) a $C_{1-3}$ alkyl group (e.g., methyl), (2) a $C_{3-10}$ cycloalkyl group (e.g., cyclopropyl), (3) a $C_{1-6}$ alkoxy group (e.g., methoxy, ethoxy) optionally substituted by 1 to 3 halogen atoms (e.g., fluorine atom), and (4) a halogen atom (e.g., fluorine atom, bromine atom);

$R^1$ and $R^2$ are each a hydrogen atom;

$R^3$ is (1) a group represented by

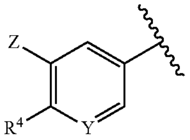

wherein $R^4$ is a $C_{1-3}$ haloalkyl group (e.g., trifluoromethyl) or a $C_{1-6}$ alkoxy group (e.g., methoxy) optionally substituted by 1 to 3 halogen atoms (e.g., fluorine atom), Y is a nitrogen atom or $CR^6$, $R^6$ is a hydrogen atom, and Z is a hydrogen atom or a halogen atom (e.g., fluorine atom).); or (2) a group represented by

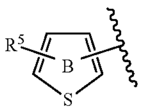

wherein $R^5$ is a $C_{1-3}$ haloalkyl group (e.g., difluoromethyl, trifluoromethyl), ring B is a thiophene ring optionally further substituted by one halogen atom (e.g., fluorine).

[Compound I-3]

The above-mentioned [compound I-2], wherein $R^3$ is a group represented by

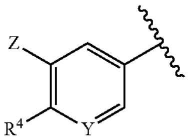

wherein $R^4$ is a $C_{1-6}$ alkoxy group (e.g., methoxy) optionally substituted by 1 to 3 halogen atoms (e.g., fluorine atom), Y is a nitrogen atom, and Z is a halogen atom (e.g., fluorine atom).

[Compound I-4]

The above-mentioned [compound I-2], wherein $R^3$ is a group represented by

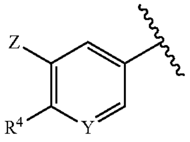

wherein $R^4$ is a $C_{1-3}$ haloalkyl group (e.g., trifluoromethyl) or a $C_{1-6}$ alkoxy group (e.g., methoxy) optionally substituted by 1 to 3 halogen atoms (e.g., fluorine atom), Y is $CR^6$, $R^6$ is a hydrogen atom, and Z is a hydrogen atom or a halogen atom (e.g., fluorine atom).

[Compound I-5]

Compound (I), wherein ring A is a benzene ring or a pyridine ring further substituted by 1 or 2 substituents selected from (1) a $C_{1-6}$ alkoxy group (e.g., methoxy), and (2) a fluorine atom;

$R^1$ and $R^2$ are each a hydrogen atom;

$R^3$ is (1) a group represented by

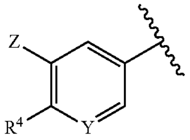

wherein $R^4$ is a $C_{1-6}$ alkoxy group (e.g., methoxy) optionally substituted by 1 to 3 halogen atoms (e.g., fluorine atom), Y is a nitrogen atom, and Z is a fluorine atom.

Specific examples of compound (I) include the compounds of the below-mentioned Examples 1-30.

As a salt of a compound represented by the formula (I), a pharmacologically acceptable salt is preferable, and examples of such salt include a salt with inorganic base, a salt with organic base, a salt with inorganic acid, a salt with organic acid, and a salt with basic or acidic amino acid.

Preferable examples of the salt with inorganic base include alkali metal salts such as sodium salt, potassium salt and the like, alkaline earth metal salts such as calcium salt, magnesium salt and the like, aluminum salt, and ammonium salt.

Preferable examples of the salt with organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine, and N,N-dibenzylethylenediamine.

Preferable examples of the salt with inorganic acid include salts with hydrogen chloride, hydrogen bromide, nitric acid, sulfuric acid, and phosphoric acid.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, and p-toluenesulfonic acid.

Preferable examples of the salt with basic amino acid include salts with arginine, lysine, and ornithine.

Preferable examples of the salt with acidic amino acid include salts with aspartic acid, and glutamic acid.

Compound (I) may be used as a prodrug.

The prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, or t-butylation);

a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation);

a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation and the like). Any of these compounds can be produced from compound (I) according to a method known per se.

The prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, a prodrug may form a salt, and as such salt, those exemplified as a salt of the compound represented by the aforementioned formula (I) can be mentioned.

Compound (I) may be labeled with an isotope (e.g., $^{3}H$, $^{13}C$, $^{14}C$, $^{18}F$, $^{35}S$, $^{125}I$) and the like.

Compound (I) labeled with or substituted by an isotope can be used, for example, as a tracer used for Positron Emission Tomography (PET) (PET tracer), and can be useful in the fields of medical diagnosis and the like.

Furthermore, compound (I) may be a hydrate or a non-hydrate, or a non-solvate, or a solvate.

Compound (I) also encompasses a deuterium conversion form wherein $^{1}H$ is converted to $^{2}H(D)$.

Furthermore, compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, and stability). The cocrystal and cocrystal salt can be produced by cocrystallization method known per se.

Compound (I) or a prodrug thereof (hereinafter sometimes to be simply abbreviated as the compound of the present invention) can be used as it is or in the form of a pharmaceutical composition (hereinafter sometimes to be abbreviated as the "medicament of the present invention") by mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As pharmacologically acceptable carriers, various organic or inorganic carrier substances conventionally used as preparation materials can be used. These can be incorporated as excipient, lubricant, binder and disintegrant for solid preparations; or solvent, solubilizing agent, suspending agent, isotonicity agent, buffer and soothing agent for liquid preparations; and the like. Where necessary, preparation additives such as preservative, antioxidant, colorant, sweetening agent and the like can be used.

Preferable examples of the excipient include lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthetic aluminum silicate and magnesium aluminometasilicate.

Preferable examples of the lubricant include magnesium stearate, calcium stearate, talc and colloidal silica.

Preferable examples of the binder include gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, laurylaminopropionic acid, lecithin, benzalkonium chloride, benzethonium chloride, glycerol monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like, polysorbates; and polyoxyethylene hydrogenated castor oil.

Preferable examples of the isotonicity agent include sodium chloride, glycerol, D-mannitol, D-sorbitol and glucose.

Preferable examples of the buffer include buffers of phosphate, acetate, carbonate, citrate etc.

Preferable examples of the soothing agent include benzyl alcohol.

Preferable examples of the preservative include p-hydroxybenzoates, chlorobutanol, benzyl alcohol, phenethyl alcohol, dehydroacetic acid and sorbic acid.

Preferable examples of the antioxidant include sulfite salts and ascorbate salts.

Preferable examples of the colorant include aqueous food tar colors (e.g., food colors such as Food Color Red Nos. 2 and 3, Food Color Yellow Nos. 4 and 5, Food Color Blue Nos. 1 and 2 and the like), water insoluble lake dyes (e.g., aluminum salt of the aforementioned aqueous food tar color), natural dyes (e.g., β-carotene, chlorophyll, red iron oxide) and the like.

Preferable examples of the sweetening agent include saccharin sodium, dipotassium glycyrrhizinate, aspartame and *stevia*.

Examples of the dosage form of the medicament of the present invention include oral preparations such as tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, aerosol, film (e.g., orally disintegrating film, oral mucosa-adhesive film), and parenteral preparations such as injection (e.g., subcutaneous injection, intravenous injection, intramuscular injection, intraperitoneal injection, drip transfusion), external preparations (e.g., transdermal absorption type preparation, ointment, lotion, adhesive preparation), suppository (e.g., rectal suppository, vaginal suppository), pellet, nasal preparation, pulmonary preparation (inhalant), eye drop, and the like. The compound of the present invention and the medicament of present invention can be administered orally or parenterally (e.g., intravenous, intraarterial, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

These preparations may be a release control preparation (e.g., sustained-release microcapsule) such as an immediate-release preparation, a sustained-release preparation and the like.

The medicament of the present invention can be produced according to a method conventionally used in the field of pharmaceutical formulation, for example, the method described in the Japanese Pharmacopoeia, and the like.

While the content of the compound of the present invention in the medicament of the present invention varies depending on the dosage form, dose of the compound of the present invention and the like, it is, for example, about 0.1 to 100 wt %.

When an oral preparation is produced, coating may be applied where necessary for the purpose of taste masking, enteric solubility or sustainability.

Examples of the coating base used for coating include sugar coating base, water-soluble film coating base, enteric film coating base, and sustained-release film coating base.

As the sugar coating base, sucrose is used, and one or more kinds selected from talc, precipitated calcium carbonate, gelatin, gum arabic, pullulan, and carnauba wax may be further used in combination.

Examples of the water-soluble film coating base include cellulose polymers such as hydroxypropylcellulose, hydroxypropylmethylcellulose, hydroxyethylcellulose, methylhydroxyethylcellulose and the like; synthetic polymers such as polyvinyl acetal diethylaminoacetate, aminoalkylmethacrylate copolymer E [Eudragit E (trade name)], polyvinylpyrrolidone and the like; and polysaccharides such as pullulan and the like.

Examples of the enteric film coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; and naturally-occurring substances such as shellac and the like.

Examples of the sustained-release film coating base include cellulose polymers such as ethylcellulose and the like; and acrylic acid polymers such as aminoalkylmethacrylate copolymer RS [Eudragit RS (trade name)], ethyl acrylate-methyl methacrylate copolymer suspension [Eudragit NE (trade name)] and the like.

Two or more kinds of the above-mentioned coating bases may be used in a mixture at an appropriate ratio. In addition, for example, light shielding agents such as titanium oxide, and red ferric oxide may also be used during coating.

The compound of the present invention has an antagonistic action on an NMDA receptor containing the NR2B subunit. As used herein, the antagonistic action on an NMDA receptor containing the NR2B subunit is confirmed by, for example, a suppressive effect on the receptor activation (e.g., glutamic acid-induced intracellular calcium ion ($Ca^{2+}$) influx).

The NMDA receptor containing the NR2B subunit is a receptor composed of four subunits in total including one NR2B subunit, and further, three subunits of 2 or 3 kinds selected from NR1, NR2A, NR2B, NR2C, NR2D, NR3A and NR3B.

The NMDA receptor containing the NR2B subunit is preferably a receptor composed of four subunits including a heterodimer of NR1 and NR2B, and a heterodimer of NR1 and one subunit selected from NR2A, NR2B, NR2C and NR2D.

The NMDA receptor containing the NR2B subunit is more preferably a receptor composed of four subunits including two sets of heterodimers of NR1 and NR2B.

Since the compound of the present invention is expected to show low toxicity (e.g., cardiotoxicity, acute toxicity, chronic toxicity, genetic toxicity, reproductive toxicity, pulmonary toxicity, carcinogenicity) and less side effects (e.g., psychotomimetic side effect), it can be used as a prophylactic or therapeutic agent, or diagnostic agent for various diseases in mammals.

The compound of the present invention is expected to show low mutagenicity in the Ames test and low hERG (human Ether-a-go-go Related Gene) inhibitory action. In addition, the compound of the present invention is expected to show less extracerebral discharge via BCRP (Breast Cancer Resistance Protein) transporter, and be superior in the stability to conjugated metabolism.

The compound of the present invention may be used as a prophylactic or therapeutic agent for central and peripheral diseases. For example, the compound of the present invention can be useful as an agent for the prophylaxis or treatment of various diseases such as (1) psychiatric diseases [e.g., major depression (including refractory major depression, treatment-resistant depression), minor depressive disorder, bipolar depression, recurrent depression, postpartum depression, stress disorder, major depressive disorder concomitant with psychosis (including delusive disorders and schizophrenia), manic or mixed mood episode, hypomanic mood episode, depression episode with atypical features, depression episode with melancholic features, depressive episodes with tonic features, depression episode after stroke (hereinafter sometimes to be simply referred to as "depression" in the present specification), dysthymic disorder, affective disorder (seasonal affective disorder and the like), delirium, peripheral symptoms of dementia (mental symptoms or behavior abnormalities), anxiety, generalized anxiety disorder, anxiety syndrome, mood disorder, cyclothymic disorder, premenstrual dysphoric disorder, panic disorder, phobia, social phobia, social anxiety disorder, obsessive disorder, post-traumatic stress syndrome, post-traumatic stress disorder, delusions or depression-type schizoaffective disorder, delusive personality disorder, Tourette syndrome, autism, fragile X syndrome, Rett syndrome, adjustment disorder, bipolar disorder (including type I bipolar disorder and type II bipolar disorder), neurosis, schizophrenia (e.g., positive symptom, negative symptom, memory disorders, delusional schizophrenia, disorganized schizophrenia, tension type schizophrenia, undifferentiated schizophrenia, remnant type schizophrenia), schizophreniform disorder, chronic fatigue syndrome, anxiety neurosis, compulsive neurosis, panic disorder, epilepsy, refractory epilepsy syndrome in children, West syndrome, anxiety, anxious mental state, emotional abnormality, cyclothymia, nervous erethism, faint, addiction, low sex drive, attention deficit hyperactivity disorder (ADHD), psychotic disturbance (e.g., short-term psychotic disorder, shared psychotic disorder), psychosis induced by alcohol, amphetamine, *cannabis*, cocaine, hallucinogen, obesity, inhalation medicine, opioids or phencyclidine, delusive disorder, Noonan syndrome, Angelman syndrome, Prader-Willi syndrome, Beckwith-Wiedemann syndrome, Silver-Russell syndrome, tuberous sclerosis, Williams syndrome, Kallmann syndrome, Rubinstein-Taybi syndrome], movement disorder, mental retardation, paranoid tendency, (2) neurodegenerative diseases [e.g., Alzheimer's disease, Alzheimer-type senile dementia, Parkinson's disease, Huntington's disease, multi-infarct dementia, frontotemporal dementia, frontotemporal dementia Parkinson's Type, alcoholic dementia or other drug related dementia, dementia associated with intracranial tumor or brain trauma, Dementia associated with Huntington's disease or Parkinson's disease, neurodegeneration accompanying brain trauma, neurodegeneration accompanying stroke, neurodegeneration accompanying cerebral infarction, neurodegeneration associated with hypoglycemia, neurodegeneration accompanying epileptic seizures, neurodegeneration accompanying neurotoxicosis, multiple system atrophy, spinal cord injury, Aids-related dementia, progressive supranuclear palsy, Pick's syndrome, Niemann-Pick syndrome, corticobasal degeneration, Down's syndrome, vascular dementia, postencephalitic parkinsonism, Lewy body dementia, HIV dementia, amyotrophic lateral sclerosis (ALS), motor neurogenesis disease (MND), Creutzfeldt-Jakob disease or prion disease, cerebral palsy, progressive supranuclear palsy, multiple sclerosis, neuromyopathy], (3) amnestic disorder, mild cognitive impairment, learning disability (e.g., reading disturbance, arithmetic disorder, dysgraphia), age-related cognition memory disorders [e.g., age-related memory disorders, senile dementia], (4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative disease and the like, (6) pain [e.g., psychogenic pain (somatoform disorder, pain disorder, somatization disorder, hypochondriasis, conversion disorder, chronic pain accompanied by depression), inflammatory pain, peripheral neuropathic pain, central neuropathic pain, neuropathic pain, acute pain, intractable pain, cancerous continuous pain, cancerous breakthrough pain, cancer pain, continuous pain, physical pain, breakthrough pain, chronic pain, tenderness, generalized pain, dull pain, dermatological pain, radiation pain, pain, postoperative thoracotomy pain syndrome], (7) deafness [e.g., kanamycin deafness, streptomycin deafness, toxic deafness, senile deafness, idiopathic bilateral sensorineural hearing loss, sudden deafness, acquired deaf mutism, genetic deafness, organic deafness, high-tone sensorineural hearing loss, occupational hearing loss, occupational hearing loss, low-tone sensorineural hearing loss], (8) traumatic brain injury, and disorder or complication associated therewith, post concussive syndrome, shaken baby syndrome, cerebral apoplexy, age-related macular degeneration, oculopalatal tremor, convulsions, phantom limb pain, radiation somnolence syndrome, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, hepatic encephalopathy, pharmacophilia, pharmacophobia, pharmacomania, drug abuse, drug dependence, drug withdrawal, migraine, stress headache, catatonic headache, diabetic neuropathy, obesity, diabetes, muscular convulsions, Meniere's disease, autonomic ataxia, alopecia, glaucoma, hypertension, cardiac disease, tachycardia, congestive cardiac failure, breathing, bronchial asthma, apnea, sudden infant death syndrome, inflammatory disease, allergic disease, systemic lupus erythematosus, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, nervous vomiting, diarrhea, constipation, postoperative ileus, and the like.

Particularly, the compound of the present invention may be useful for the prophylaxis or treatment of depression (including major depression, refractory major depression, treatment-resistant depression and the like), bipolar disorder, migraine, pain, or peripheral symptoms of dementia.

Both major depression and bipolar disorder are classified as mood disorders, and are diseases showing a depression state, or a depression state and a manic state for a long term. In recent years, it has been found that an intravenous single administration of ketamine, an NMDA receptor antagonist, improves depression symptoms accompanying major depression and bipolar disorder rapidly and in a sustained manner (Therapeutic Advances in Psychopharmacology (Ther. Adv. Psychopharmacol.), vol. 4, pp. 75-99, 2014). It has also been reported that continuous intravenous administration of CP-101, 606, which are antagonists of NMDA receptor containing the NR2B subunit, significantly improves treatment resistant-depression symptom (Journal of Clinical Psychopharmacology (J. Clin. Psychopharmacol.), vol. 28, pp. 631-637, 2008). Therefore, the compound of the present invention is promising as a prophylactic or therapeutic drug for treatment resistant-depression disease.

Migraine is a chronic and paroxysmal primary headache. While the onset mechanism is unknown, it is considered to be developed along with abnormalities of central nervous system process, abnormalities of trigeminal nerve blood vessel system and the like. In pathophysiology study of migraine, particularly aura thereof, a cortical spreading depression phenomenon is attracting attention. It has been reported that CP-101, 606 and Ro25-6981, which are antagonists of NMDA receptor containing the NR2B subunit, suppress the number of occurrence and the depth of cortical spreading depression in an experimental cortical spreading depression test using rodents (the Journal of Pharmacology and Experimental Therapeutics (J. Pharmacol. Exp. Ther.), vol. 321, pp. 564-572, 2007). Therefore, the compound of the present invention is promising as a prophylactic or therapeutic drug for migraine.

Pain is classified into acute pain in which the pain lasts for a comparatively short period of time, and chronic pain accompanying retention or recurrence for 3 months or longer, retention for not less than one month after recovery of acute tissue injury, or an unhealed lesion. An NMDA receptor containing the NR2B subunit is highly expressed in posterior horn of spinal cord which plays an important role in the acceptance of pain, and functional control thereof is suggested to enable pain control. In fact, a genetic modification operation that causes functional decline of NR2B subunit has been reported to elevate the pain sense threshold (European Journal of Neuroscience (Eur. J. Neurosci.), vol. 32, pp. 798-810, 2010). Also, it has been reported that the pain sense threshold increases due to Ifenprodil as an antagonist of an NMDA receptor containing the NR2B subunit (Pain, vol. 153, pp. 1022-1029, 2012). Therefore, the compound of the present invention is promising as a prophylactic or therapeutic drug for pain.

Dementia refers to chronic, general, and generally irreversible decline of cognition. While the degradation of quality of life of patients due to the cognitive decline is remarkable, peripheral symptoms of dementia (psychiatric symptoms or behavioral abnormalities) is also considered to be a factor markedly influencing the degradation of quality of life of patients and the caregivers of the patients. An effective therapeutic intervention method for peripheral symptoms of dementia has not been established; however, it has been reported that administration of memantine, which is an NMDA receptor antagonist, partially improves peripheral symptoms of dementia (Annals of Pharmacotherapy (Ann. Pharmacother.), vol. 42, pp. 32-38, 2007). While NMDA receptor containing the NR2B subunit is widely distributed in the brain except the cerebellum, peripheral symptoms of dementia have been reported to be related to white matter abnormality of the brain regions except the cerebellum (Journal of the Neurological Sciences (J. Neurol. Sci.), vol. 337, pp. 162-166, 2014). Therefore, the compound of the present invention is promising as a prophylactic or therapeutic drug for peripheral symptoms of dementia.

While the dose of the compound of the present invention may vary depending on the subject of administration, administration route, target disease, symptom and the like, for example, when the compound of the present invention is administered orally or parenterally to an adult patient, the dose may be, for example, generally about 0.01 to 100 mg/kg body weight per dose, preferably 0.1 to 50 mg/kg body weight per dose, and more preferably 0.5 to 20 mg/kg body weight per dose. This amount is desirably administered in one to three portions daily.

The compound of the present invention may be used in combination with other active ingredients (hereinafter to be abbreviated as concomitant drug).

Examples of the concomitant drug include the following. Acetylcholine esterase inhibitor (e.g., donepezil, rivastigmine, galanthamine, zanapezil), antidementia agent (e.g., memantine), inhibitor of β amyloid protein production, secretion, accumulation, aggregation and/or deposition, β secretase inhibitor (e.g., 6-(4-biphenylyl)methoxy-2-[2-(N,N-dimethylamino)ethyl]tetralin, 6-(4-biphenylyl)methoxy-2-(N,N-dimethylamino)methyltetralin, 6-(4-biphenylyl)methoxy-2-(N,N-dipropylamino)methyltetralin, 2-(N,N-dimethylamino)methyl-6-(4'-methoxybiphenyl-4-yl)methoxytetralin, 6-(4-biphenylyl)methoxy-2-[2-(N,N-diethylamino)ethyl]tetralin, 2-[2-(N,N-dimethylamino)ethyl]-6-(4'-methylbiphenyl-4-yl)methoxytetralin, 2-[2-(N,N-dimethylamino)ethyl]-6-(4'-methoxybiphenyl-4-yl)methoxytetralin, 6-(2',4'-dimethoxybiphenyl-4-yl)methoxy-2-[2-(N,N-dimethylamino)ethyl]tetralin, 6-[4-(1,3-benzodioxol-5-yl)phenyl]methoxy-2-[2-(N,N-dimethylamino)ethyl]tetralin, 6-(3',4'-dimethoxybiphenyl-4-yl)methoxy-2-[2-(N,N-dimethylamino)ethyl]tetralin, an optically active form thereof, a salt thereof and a hydrate thereof, OM99-2 (WO01/00663)), γ secretase inhibitor, β amyloid protein aggregation inhibitor (e.g., PTI-00703, ALZHEMED (NC-531), PPI-368 (National Publication of International Patent Application No. 11-514333), PPI-558 (National Publication of International Patent Application No. 2001-500852), SKF-74652 (Biochem. J. (1999), 340(1), 283-289)), β amyloid vaccine, β amyloid-degrading enzyme and the like, brain function enhancer (e.g., aniracetam, nicergoline), therapeutic drug for Parkinson's disease [(e.g., dopamine receptor agonist (e.g., L-DOPA, bromocriptine, pergolide, talipexole, pramipexole, cabergoline, amantadine), monoamine oxidase enzyme (MAO) inhibitor (e.g., deprenyl, selegiline, remacemide, riluzole), anticholinergic agent (e.g., trihexyphenidyl, biperiden), COMT inhibitor (e.g., entacapone)], therapeutic drug for amyotrophic lateral sclerosis (e.g., riluzole etc., neurotrophic factor), therapeutic drug for behavioral abnormalities, wandering and the like accompanying progress of dementia (e.g., sedative, antianxiety drug), apoptosis inhibitor (e.g., CPI-1189, IDN-6556, CEP-1347), neuronal differentiation/regeneration promoter (e.g., leteprinim, xaliproden; SR-57746-A), SB-216763, Y-128, VX-853, prosaptide, 5,6-dimethoxy-2-[2,2,4,6,7-pentamethyl-3-(4-methylphenyl)-2,3-dihydro-1-benzofuran-5-yl]isoindoline, 5,6-dimethoxy-2-[3-(4-isopropylphenyl)-2,2,4,6,7-pentamethyl-2,3-dihydro-1-benzofuran-5-yl]isoindoline, 6-[3-(4-isopropylphenyl)-2,2,4,6,7-pentamethyl-2,3-dihydro-1-benzofuran-5-yl]-6,7- dihydro-5H-[1,3]dioxolo[4,5-f]isoindole and an optically active form, salt or hydrate thereof), non-steroidal antiinflammatory agents (meloxicam, tenoxicam, indomethacin, ibuprofen, celecoxib, rofecoxib, aspirin, indomethacin etc.), steroid drug (dexamethasone, hexestrol, cortisone acetate etc.), disease-modifying anti-rheumatic drug (DMARDs), anti-cytokine drug (e.g., TNF inhibitor, MAP kinase inhibitor), therapeutic agent for incontinence, frequent urination (e.g., flavoxate hydrochloride, oxybutynin hydrochloride, propiverine hydrochloride), phosphodiesterase inhibitor (e.g., sildenafil(citrate)), dopamine agonist (e.g., apomorphine), antiarrhythmic drugs (e.g., mexiletine), sex hormone or a derivative thereof (e.g., progesterone, estradiol, estradiol benzoate), therapeutic agent for osteoporosis (e.g., alfacalcidol, calcitriol, elcatonin, calcitonin salmon, estriol, ipriflavone, pamidronate disodium, alendronate sodium hydrate, incadronate disodium), parathyroid hormone (PTH), calcium receptor antagonists, therapeutic drug for insomnia (e.g., benzodiazepines medicament, non-benzodiazepines medicament, melatonin agonist, orexin receptor antagonists), therapeutic drug for schizophrenia (e.g., typical antipsychotic agents such as haloperidol and the like; atypical antipsychotic agents such as clozapine, olanzapine, risperidone, aripiprazole and the like; medicament acting on metabotropic glutamate receptor or ion channel conjugated-type glutamate receptor; phosphodiesterase inhibitor), benzodiazepines medicament (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, clomipramine hydrochloride, mianserin hydrochloride, setiptilline maleate, etc.), selective serotonin reuptake inhibitor (fluvoxamine maleate, fluoxetine hydrochloride, citalopram hydrobromide, escitalopram oxalate, sertraline hydrochloride, paroxetine hydrochloride hydrate, etc.), serotonin-noradrenaline reuptake inhibitor (venlafaxine hydrochloride, duloxetine hydrochloride, desvenlafaxine, etc.), noradrenaline reuptake inhibitor (reboxetine mesylate etc.), mirtazapine, trazodone hydrochloride, bupropion hydrochloride, 5-$HT_{1A}$ agonist (buspirone hydrochloride, tandospirone citrate, osemozotan hydrocloride etc.), 5-$HT_{2A}$ antagonist, 5-$HT_{2A}$ inverse agonist, 5-$HT_3$ antagonist (cyamemazine etc.), non-cardioselective β inhibitor (propranolol hydrochloride, oxprenolol hydrochloride etc.), histamine $H_1$ antagonist, CRF antagonist, other antianxiety drug (meprobamate etc.), tachykinin antagonist, medicament that acts on metabotropic glutamate receptor, CCK antagonist, β3 adrenaline antagonist (amibegron hydrochloride etc.), GAT-1 inhibitor, N-type calcium channel inhibitor, carbonic anhydrase II inhibitor, NMDA glycine site agonist, NMDA antagonist (memantine, ketamine, esketamine, etc.), peripheral benzodiazepine receptor agonist, vasopressin receptor antagonist, phosphodiesterase inhibitor, opioid antagonist, opioid agonist, uridine, nicotinic acid receptor agonist, thyroid hormone, thyroid-stimulating hormone (TSH), thyroid-stimulating hormone release hormone (TRH), MAO inhibitor (phenelzine sulfate, tranylcypromine sulfate, moclobemide etc.), therapeutic drug for bipolar disorder (lithium carbonate, sodium valproate, lamotrigine, riluzole, felbamate etc.), cannabinoid CB1 antagonist, FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for convulsion, therapeutic drug for fibromyalgia syndrome, therapeutic drug for headache, therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for lipid abnormality such as cholesterol-lowering drug (statins), fibrate (clofibrate etc.), squalene synthetase inhibitor), therapeutic drug for behavioral abnormalities or suppressant of dromomania due to dementia (sedatives, antianxiety drug etc.), antiobesity drug, therapeutic drug for diabetes, therapeutic agent for diabetic complications, therapeutic drug for hypertension, therapeutic drug for hypotension, diuretic, chemotherapeutic agent, immunotherapeutic agent, antithrombotic agent, anti-cancer agent, antibody medicament, nucleic acid or nucleic acid derivative, aptamer drug and the like.

Two or more kinds of the above-mentioned concomitant drugs may be used in combination at an appropriate ratio.

When the compound of the present invention is applied to each of the above-mentioned diseases, it may also be used in combination with biologics (e.g., antibody medicament, nucleic acid or nucleic acid derivative, aptamer medicament, vaccine preparation), or may be used in combination with a gene therapy method and the like, or may also be used in combination with a treatment method in psychiatric field without using drugs.

Examples of the treatment method in the psychiatric field without using drug include modified electroconvulsive therapy, deep brain stimulation therapy, repetitive transcranial magnetic stimulation therapy, psychotherapy including cognitive behavioral therapy and the like.

The compound of the present invention may also be used in combination with various organ regeneration methods such as cardiac regeneration, renal regeneration, pancreatic regeneration, revascularization and the like, cell transplantation therapy utilizing bone marrow cells (bone marrow-derived mononuclear cell, myeloid stem cell), or artificial organ utilizing tissue engineering (e.g., artificial blood vessel, cardiomyocyte sheet).

By combining the compound of the present invention and a concomitant drug, a superior effect such as (1) the dose can be reduced as compared with single administration of the compound of the present invention or a concomitant drug, (2) the drug to be combined with the compound of the present invention can be selected according to the condition of patients (mild case, severe case and the like), (3) the period of treatment can be set longer by selecting a concomitant drug having different action and mechanism from the compound of the present invention, (4) a sustained treatment effect can be designed by selecting a concomitant drug having different action and mechanism from the compound of the present invention, (5) a synergistic effect can be afforded by a combined use of the compound of the present invention and a concomitant drug, and the like, may be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof may be administered to an administration subject simultaneously (the compound of the present invention and the concomitant drug may for a single preparation, or separate preparations), or may be administered at different times. For administration with time difference, the order of administration of the compound of the present invention and the concomitant drug may be any. The concomitant drug may be continuously administered for a predetermined period of time, after which the compound of the present invention may be administered.

The dosage of the concomitant drug may be determined according to the dose clinically used, and may be appropriately selected according to the administration subject, administration route, disease, combination and the like.

The dosage of the concomitant drug can be appropriately determined based on the dose employed in clinical situations. The mixing ratio of the compound of the present invention and a concomitant drug can be appropriately determined depending on the administration subject, administration route, target disease, symptom, combination, and the like.

The production method of the compound of the present invention is explained in the following.

The starting materials and reagents used in each step in the following production method, and the obtained compounds each may form a salt. Examples of the salt include those similar to the aforementioned salts of the compound of the present invention, and the like.

When the compound obtained in each step is a free compound, it can be converted to a desired salt by a method known per se. Conversely, when the compound obtained in each step is a salt, it can be converted to a free form or a desired other kind of salt by a method known per se.

The compound obtained in each step may also be used for the next reaction as a reaction mixture thereof or after obtaining a crude product thereof. Alternatively, the compound obtained in each step may be isolated and/or purified from the reaction mixture by a separation means such as concentration, crystallization, recrystallization, distillation, solvent extraction, fractionation, chromatography and the like according to a conventional method.

When the starting materials and reagent compounds of each step are commercially available, the commercially available products may be used as they are.

In the reaction of each step, while the reaction time varies depending on the reagents and solvents to be used, unless otherwise specified, it is generally 1 min-48 hr, preferably 10 min-8 hr.

In the reaction of each step, while the reaction temperature varies depending on the reagents and solvents to be used, unless otherwise specified, it is generally −78° C. to 300° C., preferably −78° C. to 150° C.

In the reaction of each step, while the pressure varies depending on the reagents and solvents to be used, unless otherwise specified, it is generally 1 atm-20 atm, preferably 1 atm-3 atm.

In the reaction of each step, for example, microwave synthesizers such as Initiator manufactured by Biotage and the like are sometimes used. While the reaction temperature varies depending on the reagents and solvents to be used, unless otherwise specified, it is generally room temperature—300° C., preferably 50° C.-250° C. While the reaction time varies depending on the reagents and solvents to be used, unless otherwise specified, it is generally 1 min-48 hr, preferably 1 min-8 hr.

In the reaction of each step, unless otherwise specified, a reagent is used in 0.5 equivalent-20 equivalents, preferably 0.8 equivalent-5 equivalents, relative to the substrate. When a reagent is used as a catalyst, the reagent is used in 0.001 equivalent-1 equivalent, preferably 0.01 equivalent-0.2 equivalent, relative to the substrate. When the reagent is also a reaction solvent, the reagent is used in a solvent amount.

In the reaction of each step, unless otherwise specified, it is performed without solvent or by dissolving or suspending in a suitable solvent. Specific examples of the solvent include those described in Examples and the following.

alcohols: methanol, ethanol, tert-butyl alcohol, 2-methoxyethanol and the like;

ethers: diethyl ether, diphenyl ether, tetrahydrofuran, 1,2-dimethoxyethane and the like;

aromatic hydrocarbons: chlorobenzene, toluene, xylene and the like;

saturated hydrocarbons: cyclohexane, hexane and the like;

amides: N,N-dimethylformamide, N-methylpyrrolidone and the like;

halogenated hydrocarbons: dichloromethane, carbon tetrachloride and the like;

nitriles: acetonitrile and the like;

sulfoxides: dimethyl sulfoxide and the like;

aromatic organic bases: pyridine and the like;

acid anhydrides: acetic anhydride and the like;

organic acids: formic acid, acetic acid, trifluoroacetic acid and the like;

inorganic acids: hydrochloric acid, sulfuric acid and the like; esters: ethyl acetate and the like;

ketones: acetone, methyl ethyl ketone and the like; and water.

Two or more kinds of the above-mentioned solvents may be used by mixing at an appropriate ratio.

When a base is used in the reaction of each step, for example, bases shown below or those described in Examples are used.

inorganic bases: sodium hydroxide, magnesium hydroxide, sodium carbonate, calcium carbonate, sodium hydrogen carbonate and the like;

organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;

metal alkoxides: sodium ethoxide, potassium tert-butoxide and the like;

alkali metal hydrides: sodium hydride and the like;

metal amides: sodium amide, lithium diisopropyl amide, lithium hexamethyldisilazide and the like; and organic lithiums: n-butyllithium and the like.

When an acid or acidic catalyst is used in the reaction of each step, for example, acids and acidic catalysts shown below or those described in Examples are used.

inorganic acids: hydrochloric acid, sulfuric acid, nitric acid, hydrobromic acid, phosphoric acid and the like;

organic acids: acetic acid, trifluoroacetic acid, citric acid, p-toluenesulfonic acid, 10-camphorsulfonic acid and the like; and Lewis acids: boron trifluoride diethyl ether complex, zinc iodide, anhydrous aluminum chloride, anhydrous zinc chloride, anhydrous iron chloride and the like.

Unless otherwise specified, the reaction of each step is performed according to a method known per se, for example, the methods described in Jikken Kagaku Kouza 5th edition, vol. 13-vol. 19 (The Chemical Society of Japan ed.); Shinjikken Kagaku Kouza (Courses in Experimental Chemistry), vol. 14-vol. 15 (The Chemical Society of Japan ed.); Fine Organic Chemistry rev. 2nd edition (L. F. Tietze, Th. Eicher, NANKODO); rev. Organic Name Reactions, Their Mechanism and Essence (Hideo Togo, Kodansha); ORGANIC SYNTHESES Collective Volume I-VII (John Wiley & Sons Inc); Modern Organic Synthesis in the Laboratory, A Collection of Standard Experimental Procedures (Jie Jack Li, OXFORD UNIVERSITY); Comprehensive Heterocyclic Chemistry III, Vol. 1-Vol. 14 (Elsevier Japan KK); Strategic Applications of Named Reactions in Organic Synthesis (translation supervisor Kiyoshi Tomioka, KAGAKUDOJIN); Comprehensive Organic Transformations (VCH Publishers Inc.), 1989 and the like, or the methods described in the Examples.

In each step, protection or deprotection reaction of a functional group is performed by the method known per se, for example, the methods described in "Protective Groups in Organic Synthesis, 4th Ed." (Theodora W. Greene, Peter G. M. Wuts) Wiley-Interscience, 2007; "Protecting Groups 3rd Ed." (P. J. Kocienski) Thieme, 2004 and the like, or the methods described in the Examples.

Examples of the protecting group of the hydroxyl group of alcohol and the like and a phenolic hydroxyl group include ether protecting groups such as methoxymethyl ether, benzyl ether, tert-butyldimethylsilyl ether, tetrahydropyranyl ether and the like; carboxylate ester protecting groups such as acetate ester and the like; sulfonate ester protecting groups such as methanesulfonate ester and the like; carbonate ester protecting groups such as tert-butylcarbonate and the like, and the like.

Examples of the protecting group of the carbonyl group of aldehyde include acetal protecting groups such as dimethyl acetal and the like; cyclic acetal protecting groups such as 1,3-dioxane and the like, and the like.

Examples of the protecting group of the carbonyl group of ketone include ketal protecting groups such as dimethyl ketal and the like; cyclic ketal protecting groups such as 1,3-dioxane and the like; oxime protecting groups such as O-methyloxime and the like; hydrazone protecting groups such as N,N-dimethylhydrazone and the like, and the like.

Examples of the carboxyl protecting group include ester protecting groups such as methyl ester and the like; amide protecting groups such as N,N-dimethylamide and the like, and the like.

Examples of the thiol protecting group include ether protecting groups such as benzyl thioether and the like; ester protecting groups such as thioacetate ester, thiocarbonate, thiocarbamate and the like, and the like.

Examples of the protecting group of an amino group and an aromatic heterocycle such as imidazole, pyrrole, indole and the like include carbamate protecting groups such as benzyl carbamate and the like; amide protecting groups such as acetamide and the like; alkylamine protecting groups such as N-triphenylmethylamine and the like, sulfonamide protecting groups such as methanesulfonamide and the like, and the like.

The protecting group can be removed by a method known per se, for example, a method using acid, base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), a reduction method and the like.

When a reduction reaction is performed in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When a carbon-carbon double bond or triple bond is reduced, a method using a catalyst such as palladium-carbon, Lindlar catalyst and the like is used.

When an oxidation reaction is performed in each step, examples of an oxidizing agent to be used include peracids such as m-chloroperbenzoic acid (mCPBA), hydrogen peroxide, tert-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; high valent iodine reagents such as iodosylbenzene and the like; reagents containing manganese such as manganese dioxide, potassium permanganate and the like; leads such as lead tetraacetate and the like; reagents containing chrome such as pyridinium chlorochromate (PCC), pyridinium dichromate (PDC), Jones reagent and the like; halogen compounds such as N-bromosuccinimide (NBS) and the like; oxygen; ozone; sulfur trioxide pyridine complex; osmium tetraoxide; selenium dioxide; 2,3-dichloro-5,6-dicyano-1,4-benzoquinone (DDQ) and the like.

When a radical cyclization reaction is performed in each step, examples of the radical initiator to be used include azo compounds such as azobisisobutyronitrile (AIBN) and the like; water-soluble radical initiators such as 4,4'-azobis-4-cyanopentanoic acid (ACPA) and the like; triethylboron in the presence of air or oxygen; benzoyl peroxide and the like. In addition, examples of the radical reaction agent to be used include tributylstannane, tristrimethylsilylsilane, 1,1,2,2-tetraphenyldisilane, diphenylsilane, samarium iodide and the like.

When the Wittig reaction is performed in each step, examples of the Wittig reagent to be used include alkylidenephosphoranes and the like. Alkylidenephosphoranes can be prepared by a method known per se, for example, by reacting a phosphonium salt with a strong base.

When the Horner-Emmons reaction is performed in each step, examples of the reagent to be used include phosphonoacetic acid esters such as methyl dimethylphosphonoacetate, ethyl diethylphosphonoacetate and the like; and bases such as alkali metal hydrides, organic lithiums and the like.

When the Friedel-Crafts reaction is performed in each step, examples of the reagent to be used include a combination of Lewis acid and acid chloride or a combination of Lewis acid and alkylating agents (e.g., alkyl halides, alcohol, olefins and the like). Alternatively, an organic acid and an inorganic acid can also be used instead of the Lewis acid, and acid anhydride such as acetic anhydride and the like can also be used instead of acid chloride.

When an aromatic nucleophilic substitution reaction is performed in each step, a nucleophilic agent (e.g., amines, imidazole and the like) and a base (e.g., organic bases and the like) are used as the reagent.

When a nucleophilic addition reaction with carbanion, a nucleophilic 1,4-addition reaction with carbanion (Michael addition reaction) or a nucleophilic substitution reaction with carbanion is performed in each step, examples of the base to be used for developing carbanion include organic lithiums, metal alkoxides, inorganic bases, organic bases and the like.

When the Grignard reaction is performed in each step, examples of the Grignard reagent include aryl magnesium halides such as phenyl magnesium bromide and the like; and alkyl magnesium halides such as methyl magnesium bromide and the like. The Grignard reagent can be prepared by a method known per se, for example, by reacting alkyl halide or aryl halide with metal magnesium in ether or tetrahydrofuran as a solvent.

When the Knoevenagel condensation reaction is performed in each step, an active methylene compound held between two electron-withdrawing groups (e.g., malonic acid, diethyl malonate, malononitrile and the like) and a base (e.g., organic bases, metal alkoxides, inorganic bases) are used as the reagents.

When the Vilsmeier-Haack reaction is performed in each step, phosphoryl chloride and an amide derivative (e.g., N,N-dimethylformamide and the like) are used as the reagents.

When an azidation reaction of alcohols, alkyl halides or sulfonate esters is performed in each step, examples of the azidation agent to be used include diphenylphosphoryl azide (DPPA), trimethylsilyl azide, sodium azide and the like. For example, when alcohols are azidated, a method using diphenylphosphoryl azide and 1,8-diazabicyclo[5.4.0]undec-7-ene (DBU), a method using trimethylsilyl azide and the Lewis acid and the like can be employed.

When a reductive amination reaction is performed in each step, examples of the reducing agent to be used include sodium triacetoxyborohydride, sodium cyanoborohydride, hydrogen, formic acid and the like. When the substrate is an amine compound, examples of the carbonyl compound to be used besides para-formaldehyde include aldehydes such as acetaldehyde and the like, ketones such as cyclohexanone and the like. When the substrate is a carbonyl compound, examples of the amines to be used include ammonia; primary amines such as methylamine and the like; secondary amines such as dimethylamine and the like, and the like.

When the Mitsunobu reaction is performed in each step, azodicarboxylate esters (e.g., diethyl azodicarboxylate (DEAD), diisopropyl azodicarboxylate (DIAD) and the like) and phosphines such as triphenylphosphine, tributylphosphine and the like are used as the reagents.

When an esterification reaction, amidation reaction or ureation reaction is performed in each step, examples of the reagent to be used include halogenated acyl forms such as acid chloride, acid bromide and the like; and activated carboxylic acids such as acid anhydride, active ester form, sulfuric acid ester form and the like. Examples of the carboxylic acid activator include carbodiimide condensing agents such as N-(3-(dimethylamino)propyl)-N'-ethylcarbodiimide hydrochloride (WSC·HCl) and the like; triazine condensing agents such as 4-(4,6-dimethoxy-1,3,5-triazin-2-yl)-4-methylmorpholinium chloride-n-hydrate (DMT-MM) and the like; carbonate ester condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methylpyridinium iodide (Mukaiyama reagent); thionyl chloride; lower alkyl haloformates such as ethyl chloroformate and the like; 0-(7-azabenzotriazol-1-yl)-N,N,N',N'-tetramethyluronium hexafluorophosphate (HATU); sulfuric acid; a combination thereof and the like. When a carbodiimide condensing agent is used, additives such as 1-hydroxybenzotriazole (HOBt), N-hydroxysuccinimide (HOSu), dimethylaminopyridine (DMAP) and the like can be further added to the reaction.

When a coupling reaction is performed in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride and the like; nickel compounds such as tetrakis(triphenylphosphine)nickel(0) and the like; rhodium compounds such as tris(triphenylphosphine)rhodium(III) chloride and the like; a cobalt compound; copper compounds such as copper oxide, copper(I) iodide and the like; a platinum compound and the like. A base may be further added to the reaction and examples of such base include inorganic bases and the like.

When a thiocarbonylation reaction is performed in each step, diphosphorus pentasulfide is representatively used as a thiocarbonylating agent. Besides diphosphorus pentasulfide, a reagent having a 1,3,2,4-dithiadiphosphetane-2,4-disulfide structure such as 2,4-bis(4-methoxyphenyl-1,3,2,4-dithiadiphosphetane-2,4-disulfide (Lawesson reagent) and the like may also be used.

When the Wohl-Ziegler reaction is performed in each step, examples of the halogenating agent to be used include N-iodosuccinimide, N-bromosuccinimide (NBS), N-chlorosuccinimide (NCS), bromine, sulfuryl chloride and the like. Furthermore, the reaction can be accelerated by adding heat, light, radical initiators such as benzoyl peroxide, azobisisobutyronitrile and the like to the reaction.

When a halogenating reaction of a hydroxy group is performed in each step, examples of the halogenating agent to be used include hydrohalic acid and acid halide of inorganic acid; specifically, hydrochloric acid, thionyl chloride, phosphorus oxychloride and the like for chlorination, and 48% hydrobromic acid and the like for bromination. In addition, a method of obtaining an alkyl halide form from alcohol by reacting with triphenylphosphine and carbon tetrachloride or carbon tetrabromide, and the like may be used. Alternatively, a method of synthesizing an alkyl halide form via a two-step reaction including conversion of alcohol to sulfonic acid ester, and reacting same with lithium bromide, lithium chloride or sodium iodide may also be used.

When the Arbuzov reaction is performed in each step, examples of the reagent to be used include alkyl halides such as ethyl bromoacetate and the like; and phosphites such as triethyl phosphite, tri(isopropyl) phosphite and the like.

When a sulfonate esterification reaction is performed in each step, examples of the sulfonylating agent to be used include methanesulfonyl chloride, p-toluenesulfonyl chloride, methanesulfonic anhydride, p-toluenesulfonic anhydride and the like.

When a hydrolysis reaction is performed in each step, an acid or a base is used as the reagent. In addition, when an acid hydrolysis reaction of tert-butyl ester is performed, formic acid, triethylsilane and the like are sometimes added to reductively trap the by-produced tert-butyl cation.

When a dehydration reaction is performed in each step, examples of the dehydrating agent to be used include sulfuric acid, phosphorus pentoxide, phosphorus oxychloride, N,N'-dicyclohexylcarbodiimide, alumina, polyphosphoric acid and the like.

Compound (I) can be produced from compound (1) by the following production step A, or a method analogous thereto.

[production step A]

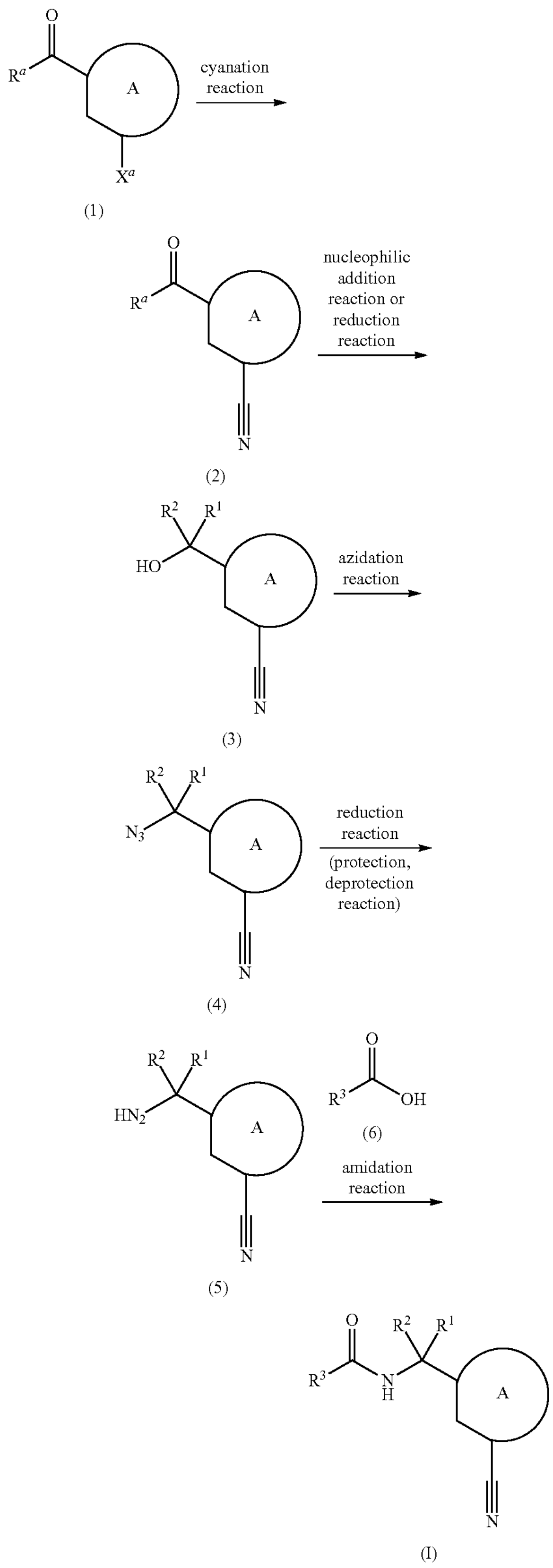

(1) (2) (3) (4) (5) (6) (I)

wherein $R^a$ is a hydrogen atom or a $C_{1-3}$ alkyl group optionally substituted by a $C_{1-6}$ alkoxy group or a fluorine atom, $X^a$ is a halogen atom, and ring A, $R^1$, $R^2$, and $R^3$ are as defined above.

Compound (2) can be produced by subjecting compound (1) to a cyanation reaction. The cyanation reagent to be used includes zinc cyanide and the like and as the metal catalyst to be used includes tetrakis(triphenylphosphine)palladium (0) and the like. Compound (3) can be produced by subjecting compound (2) to a nucleophilic addition reaction by carbanion or reduction reaction. The reagent to be used for the nucleophilic addition reaction includes organic lithium reagent, Grignard reagent (organic magnesium halide) and the like. Compound (4) can be produced by subjecting compound (3) to an azidation reaction. Compound (5) can be produced by subjecting compound (4) to a reduction reaction. The reagent to be used includes triphenylphosphine and the like. In addition, compound (5) can be produced by subjecting compound (4) to a reduction reaction, followed by introduction of a protecting group and a deprotection reaction. The protecting group includes tert-butoxycarbonyl group and the like. Compound (I) can be produced by subjecting compound (5) to an amidation reaction with compound (6).

Compound (I) can also be produced from compound (7) by the following production step B, or a method analogous thereto.

[Production step B]

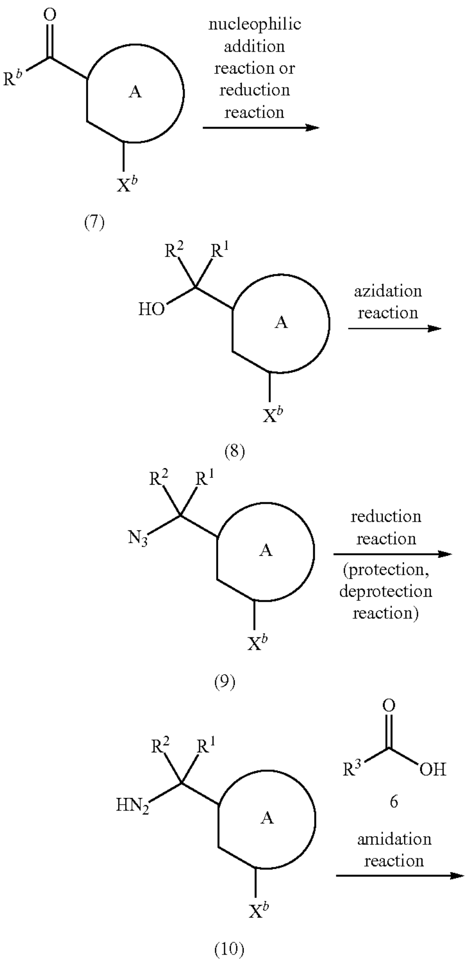

(7) (8) (9) (10)

-continued

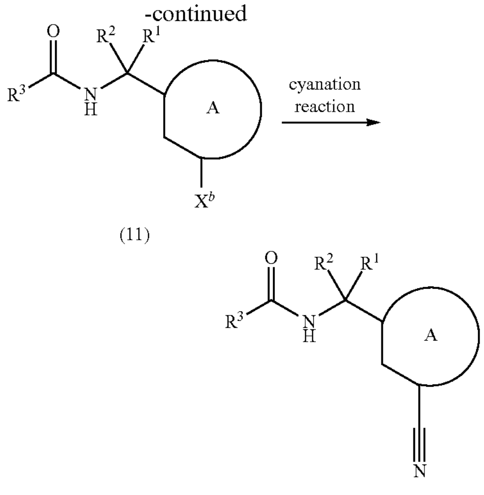

(11)

(I)

wherein $R^b$ is a hydrogen atom or a $C_{1-3}$ alkyl group optionally substituted by a $C_{1-6}$ alkoxy group or a fluorine atom, $X^b$ is a halogen atom, and ring A, $R^1$, $R^2$, and $R^3$ are as defined above.

Compound (8) can be produced by subjecting compound (7) to a nucleophilic addition reaction by carbanion or reduction reaction. Compound (9) can be produced by subjecting compound (8) to an azidation reaction. Compound (10) can be produced by subjecting compound (9) to a reduction reaction. In addition, compound (10) can be produced by subjecting compound (9) to a reduction reaction, followed by introduction of a protecting group and a deprotection reaction. Compound (11) can be produced by subjecting compound (10) to an amidation reaction with compound (6). Compound (I) can be produced by subjecting compound (11) to a cyanation reaction.

Each step of production step B can be performed by a method similar to each step of production step A.

In the thus-obtained compound (I), an intramolecular functional group can also be converted to an object functional group by combining chemical reactions known per se. Examples of the chemical reaction include oxidation reaction, reduction reaction, alkylation reaction, acylation reaction, ureation reaction, hydrolysis reaction, amination reaction, esterification reaction, aryl coupling reaction, deprotection reaction and the like.

Compound (I) obtained by the above-mentioned production method can be isolated and purified by a known means, such as solvent extraction, pH change of solution, phase transfer, crystallization, recrystallization, chromatography and the like.

When compound (I) has an optical isomer, a stereoisomer, a regioisomer or a rotamer, these are also encompassed in compound (I), and can be obtained as a single product according to synthesis and separation methods known per se. For example, when compound (I) contains an optical isomer, an optical isomer resolved from this compound is also encompassed in compound (I).

The optical isomer can be produced according to a method known per se.

Compound (I) may be a crystal.

A crystal of compound (I) (hereinafter sometimes to be abbreviated as the crystal of the present invention) can be produced by crystallization, by applying a crystallization method known per se.

The crystal of the present invention is superior in the physicochemical properties (e.g., melting point, solubility, stability) and biological properties (e.g., pharmacokinetics (absorbability, distribution, metabolism, excretion), efficacy), and is expected to be useful as a medicament.

EXAMPLE

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

Unless particularly indicated, the elution in column chromatography in the Examples was performed under observation by TLC (Thin Layer Chromatography). For TLC observation, $60F_{254}$ manufactured by Merck was used as a TLC plate, and the solvent used as an elution solvent for column chromatography was used as eluent. For detection, moreover, a UV detector was adopted. In silica gel column chromatography, the notation of NH means use of aminopropylsilane-bonded silica gel. In preparative HPLC (high performance liquid chromatography), the indication of C18 means use of octadecyl-bonded silica gel. The ratio shown for elution solvents is, unless otherwise specified, a volume mixing ratio.

For the analysis of $^1H$ NMR, ACD/SpecManager (trade name) software and the like were used. Very mild peaks for protons of a hydroxy group, an amino group and the like are sometimes not described.

MS was measured by LC/MS. As ionization method, ESI method, or APCI method was used. The data indicates those found. Generally, molecular ion peaks are observed; however, they may be observed as a fragment ion. In the case of a salt, generally, a molecular ion peak or a fragment ion peak of a free form is observed.

The elemental analytical value (Anal.) shows Calculated value (Calcd) and Found value (Found).

In the following Examples, the following abbreviations are used.

mp: melting point
MS: mass spectrum
M: mol concentration
$CDCl_3$: deuterochloroform
DMSO-$d_6$: deuterodimethyl sulfoxide
$^1H$ NMR: proton nuclear magnetic resonance
LC/MS: liquid chromatograph mass spectrometer
ESI: electrospray ionization
APCI: atmospheric pressure chemical ionization
HATU: O-(7-azabenzotriazol-1-yl)-N,N,N',N'-tetramethyluronium hexafluorophosphate
DPPA: diphenyl phosphorazidate
TFA: trifluoroacetic acid
DIPEA: N-ethyl-N-isopropylpropan-2-amine
DMA: N,N-dimethylacetamide
DMF: N,N-dimethylformamide
HOBt: 1H-benzotriazol-1-ol
HOBt-$H_2O$: 1H-benzotriazol-1-ol monohydrate
THF: tetrahydrofuran
WSC·HCl: N-(3-(dimethylamino)propyl)-N'-ethylcarbodiimide hydrochloride
$Boc_2O$: di-tert-butyl dicarbonate
DBU: 2,3,4,6,7,8,9,10-octahydropyrimido[1,2-a]azepine
TEA: triethylamine
$Pd(PPh_3)_4$: tetrakis (triphenylphosphine)palladium (0)

Example 1

N-[(2-bromo-5-cyanophenyl)methyl]-3-fluoro-4-(trifluoromethoxy)benzamide

A) 3-(azidomethyl)-4-bromobenzonitrile

To a mixture of 4-bromo-3-(hydroxymethyl)benzonitrile (3.42 g), DBU (4.86 ml) and THF (35 ml) was added DPPA (6.94 mL) at 0° C., and the mixture was stirred at room temperature for 4 hr. Water was added to the reaction mixture, and the mixture was extracted with ethyl acetate. The organic layer was washed with water and saturated brine, dried over anhydrous sodium sulfate, and concentrated under reduced pressure. The residue was purified by silica gel column chromatography (ethyl acetate/hexane) to give the title compound (3.71 g).

$^1$H NMR (300 MHz, DMSO-$d_6$) δ 4.63 (2H, s), 7.76-7.82 (1H, m), 7.94 (1H, d, J=8.3 Hz), 8.02 (1H, d, J=2.3 Hz).

B) 3-(aminomethyl)-4-bromobenzonitrile

To a mixture of 3-(azidomethyl)-4-bromobenzonitrile (3.71 g), THF (40 ml) and water (10 ml) was added triphenylphosphine (4.52 g) at room temperature, and the mixture was stirred at room temperature overnight. The mixture was concentrated under reduced pressure, and the residue was purified by silica gel column chromatography (NH, ethyl acetate/hexane) to give the title compound (2.87 g).

$^1$H NMR (300 MHz, DMSO-$d_6$) δ 1.99 (2H, br s), 3.76 (2H, s), 7.64 (1H, dd, J=8.1, 2.1 Hz), 7.80 (1H, d, J=8.3 Hz), 7.96-7.99 (1H, m).

C) N-[(2-bromo-5-cyanophenyl)methyl]-3-fluoro-4-(trifluoromethoxy)benzamide

A mixture of 3-(aminomethyl)-4-bromobenzonitrile (0.301 g), DMF (2 ml), 3-fluoro-4-(trifluoromethoxy)benzoic acid (0.032 g), TEA (0.398 ml) and HATU (0.814 g) was stirred at room temperature overnight. Water was added to the reaction mixture, and the mixture was extracted with ethyl acetate. The organic layer was washed with water and saturated brine, dried over anhydrous sodium sulfate, and concentrated under reduced pressure. The residue was purified by silica gel column chromatography (ethyl acetate/hexane) to give the title compound (0.562 g).

$^1$H NMR (300 MHz, DMSO-$d_6$) δ 4.54 (2H, d, J=5.6 Hz), 7.69-7.90 (5H, m), 8.03 (1H, dd, J=11.3, 1.9 Hz), 9.25 (1H, t, J=5.6 Hz).

Example 7

N-[(5-cyano-2-methoxyphenyl)methyl]-6-(difluoromethoxy)-5-fluoropyridine-3-carboxamide A) N-[(5-bromo-2-methoxyphenyl)methyl]-6-(difluoromethoxy)-5-fluoropyridine-3-carboxamide A mixture of 6-(difluoromethoxy)-5-fluoronicotinic acid (1.04 g), DMF (10 ml), (5-bromo-2-methoxyphenyl)methanamine (1.08 g), TEA (1.39 ml) and HATU (2.85 g) was stirred at room temperature for 1 hr. Water was added to the reaction mixture, and the mixture was extracted with ethyl acetate. The organic layer was washed with water and saturated brine, dried over anhydrous sodium sulfate, and concentrated under reduced pressure. The residue was purified by silica gel column chromatography (ethyl acetate/hexane) to give the title compound (1.51 g).

$^1$H NMR (300 MHz, DMSO-$d_6$) δ 3.83 (3H, s), 4.44 (2H, d, J=6.0 Hz), 6.99 (1H, d, J=9.0 Hz), 7.34 (1H, d, J=2.6 Hz), 7.43 (1H, dd, J=8.8, 2.4 Hz), 7.55-8.05 (1H, m), 8.34 (1H, dd, J=10.5, 1.9 Hz), 8.60 (1H, d, J=1.9 Hz), 9.10 (1H, t, J=5.6 Hz).

B) N-[(5-cyano-2-methoxyphenyl)methyl]-6-(difluoromethoxy)-5-fluoropyridine-3-carboxamide A mixture of N-[(5-bromo-2-methoxyphenyl)methyl]-6-(difluoromethoxy)-5-fluoropyridine-3-carboxamide (0.810 g), $Pd(PPh_3)_4$ (0.231 g), zinc cyanide (0.352 g) and DMF (12 ml) was microwave irradiated at 110° C. for 1 hr. The mixture was purified by silica gel column chromatography (NH, ethyl acetate/hexane) to give the title compound (0.242 g).

$^1$H NMR (300 MHz, DMSO-$d_6$) δ 3.92 (3H, s), 4.46 (2H, d, J=5.6 Hz), 7.20 (1H, d, J=8.7 Hz), 7.51-8.08 (3H, m), 8.35 (1H, dd, J=10.9, 1.9 Hz), 8.61 (1H, d, J=1.9 Hz), 9.13 (1H, s).

Example 9

N-[(5-cyano-2-methoxypyridin-3-yl)methyl]-6-(difluoromethoxy)-5-fluoropyridine-3-carboxamide A) 5-formyl-6-methoxypyridine-3-carbonitrile A mixture of 5-bromo-2-methoxynicotinaldehyde (1.70 g), $Pd(PPh_3)_4$ (0.909 g), zinc cyanide (1.386 g) and DMF (14 ml) was microwave irradiated at 110° C. for 1 hr. The same reaction was performed once more (total 2 batches). The mixtures were combined and filtered. The filtrate was concentrated and the residue was purified by silica gel column chromatography (ethyl acetate/hexane) to give the title compound (2.16 g).

$^1$H NMR (300 MHz, DMSO-$d_6$) δ 4.10 (3H, s), 8.53 (1H, d, J=2.3 Hz), 8.97 (1H, d, J=2.6 Hz), 10.18 (1H, s).

B) 5-(hydroxymethyl)-6-methoxypyridine-3-carbonitrile

To a mixture of 5-formyl-6-methoxypyridine-3-carbonitrile (2.15 g) and ethanol (25 ml) was added sodium tetrahydroborate (0.752 g) at 0° C. The mixture was stirred at room temperature for 1 hr. To the reaction mixture was added saturated aqueous ammonium chloride solution at 0° C., and the mixture was extracted with ethyl acetate. The organic layer was washed with water and saturated brine, dried over anhydrous magnesium sulfate, and concentrated under reduced pressure to give the title compound (2.18 g).

MS: $[M+H]^+$ 165.1.

C) 5-(azidomethyl)-6-methoxypyridine-3-carbonitrile

A mixture of 5-(hydroxymethyl)-6-methoxypyridine-3-carbonitrile (2.15 g), DPPA (5.91 mL), DBU (4.15 mL) and THF (30 ml) was stirred at room temperature overnight. The mixture was concentrated under reduced pressure, and the residue was purified by silica gel column chromatography (ethyl acetate/hexane) to give the title compound (2.63 g).

MS: $[M+H]^+$ 190.1.

D) 5-(aminomethyl)-6-methoxypyridine-3-carbonitrile

A mixture of 5-(azidomethyl)-6-methoxypyridine-3-carbonitrile (2.50 g), triphenylphosphine (4.16 g), THF (20 ml) and water (5 ml) was stirred at room temperature overnight. The mixture was concentrated under reduced pressure, and the residue was purified by silica gel column chromatography (methanol/ethyl acetate) to give the title compound (1.50 g).

MS: $[M+H]^+$ 164.1.

E) N-[(5-cyano-2-methoxypyridin-3-yl)methyl]-6-(difluoromethoxy)-5-fluoropyridine-3-carboxamide A mixture of 6-(difluoromethoxy)-5-fluoronicotinic acid (1.87 g), 5-(aminomethyl)-6-methoxypyridine-3-carbonitrile (1.47 g), WSC·HCl (2.59 g), HOBt (1.46 g), TEA (3.77 ml) and DMF (20 ml) was stirred at room temperature overnight. Water was added to the reaction mixture, and the precipitated solid was collected by filtration and recrystallized from ethyl acetate/hexane to give the title compound (2.73 g).

1H NMR (300 MHz, DMSO-$d_6$) δ 4.01 (3H, s), 4.43 (2H, br s), 7.56-8.14 (2H, m), 8.35 (1H, dd, J=10.5, 1.9 Hz), 8.62 (2H, dd, J=8.3, 1.9 Hz), 9.21 (1H, brs).

Example 12

N-[(5-cyano-2-fluorophenyl)methyl]-6-(difluoromethoxy)-5-fluoropyridine-3-carboxamide A) 3-(azidomethyl)-4-fluorobenzonitrile To a mixture of 4-fluoro-3-(hydroxymethyl)benzonitrile (0.507 g) and THF (6 ml) were added DBU (0.758 ml) and DPPA (0.865 mL) at 0° C. The mixture was stirred at room temperature for 5 hr, and concentrated under reduced pressure. The residue was purified by silica gel column chromatography (ethyl acetate/hexane) to give the title compound (0.533 g).

1H NMR (300 MHz, DMSO-$d_6$) δ 4.59 (2H, s), 7.54 (1H, dd, J=9.4, 8.7 Hz), 7.94-8.02 (1H, m), 8.05 (1H, dd, J=6.8, 1.9 Hz).

B) tert-butyl [(5-cyano-2-fluorophenyl)methyl]carbamate

To a mixture of 3-(azidomethyl)-4-fluorobenzonitrile (0.531 g), THF (10 ml) and water (0.5 ml) was added triphenylphosphine (0.870 g) at 0° C. The mixture was stirred at room temperature for 18 hr, $Boc_2O$ (0.770 mL) was added, and the mixture was stirred at room temperature for 30 min. The mixture was concentrated under reduced pressure, and the residue was purified by silica gel column chromatography (ethyl acetate/hexane) to give the title compound (0.602 g).

$^1H$ NMR (300 MHz, DMSO-$d_6$) δ 1.39 (9H, s), 4.20 (2H, br d, J=6.0 Hz), 7.38-7.55 (2H, m), 7.69-7.79 (1H, m), 7.81-7.90 (1H, m).

C) 3-(aminomethyl)-4-fluorobenzonitrile hydrochloride

To a mixture of tert-butyl [(5-cyano-2-fluorophenyl)methyl]carbamate (0.600 g) and ethyl acetate (7 ml) was added 4 M hydrogen chloride/ethyl acetate (8.99 ml) at 0° C. The mixture was stirred at room temperature for 20 hr, and the precipitated solid was collected by filtration and washed with ethyl acetate to give the title compound (0.409 g).

MS: $[M+H]^+$ 151.4.

D) N-[(5-cyano-2-fluorophenyl)methyl]-6-(difluoromethoxy)-5-fluoropyridine-3-carboxamide A mixture of 6-(difluoromethoxy)-5-fluoronicotinic acid (0.111 g), DMF (3 ml), 3-(aminomethyl)-4-fluorobenzonitrile hydrochloride (0.100 g), DIPEA (0.281 ml), WSC·HCl (0.134 g) and HOBt (0.094 g) was stirred at room temperature for 3 hr. Water was added to the reaction mixture, and the precipitated solid was collected by filtration and washed with water to give the title compound (0.142 g).

$^1H$ NMR (300 MHz, DMSO-$d_6$) δ 4.55 (2H, br s), 7.47 (1H, dd, J=10.0, 8.5 Hz), 7.80 (1H, t, J=72.0 Hz), 7.83-7.98 (2H, m), 8.33 (1H, dd, J=10.7, 2.1 Hz), 8.59 (1H, d, J=2.3 Hz), 9.29 (1H, br s).

Example 16

N-[(5-cyano-2-methoxypyridin-3-yl)methyl]-5-(trifluoromethyl)thiophene-2-carboxamide A mixture of 5-(trifluoromethylthiophene)-2-carboxylic acid (0.105 g), 5-(aminomethyl)-6-methoxypyridine-3-carbonitrile (0.087 g), WSC·HCl (0.153 g), HOBt (0.086 g), TEA (0.223 ml) and DMF (20 ml) was stirred at room temperature overnight. Water was added to the reaction mixture, and the mixture was extracted with ethyl acetate. The organic layer was washed with water and saturated brine, dried over anhydrous magnesium sulfate, and concentrated under reduced pressure. The residue was purified by silica gel column chromatography (ethyl acetate/hexane) to give the title compound (0.072 g).

$^1H$ NMR (300 MHz, DMSO-$d_6$) δ4.01 (3H, s), 4.41 (2H, s), 7.80 (1H, dd, J=4.1, 1.1 Hz), 7.91 (1H, dd, J=4.1, 1.1 Hz), 8.05 (1H, d, J=2.3 Hz), 8.64 (1H, d, J=1.9 Hz), 9.32 (1H, br s).

Example 17

N-[(3-cyano-2-fluoro-6-methoxyphenyl)methyl]-6-(difluoromethoxy)-5-fluoropyridine-3-carboxamide A) 2-fluoro-3-formyl-4-methoxybenzonitrile To a mixture of diisopropylamine (11.1 ml) and THF (100 ml) was added 1.6 M butyllithium hexane solution (45.5 ml) at −78° C. over 10 min, and the mixture was stirred at 0° C. for 20 min. The mixture was cooled to −78° C. and 2-fluoro-4-methoxybenzonitrile (10.0 g) was added. The mixture was stirred at −78° C. for 1 hr and DMF (15.4 ml) was added. The mixture was stirred at −78° C. for 1 hr and the reaction was discontinued by adding ethyl acetate and 2 M hydrochloric acid. The mixture was extracted with ethyl acetate. The organic layer was washed with saturated brine, dried over anhydrous sodium sulfate, filtered, and concentrated under reduced pressure. The obtained solid was recrystallized from ethyl acetate/heptane to give the title compound (8.60 g).

$^1$H NMR (300 MHz, DMSO-$d_6$) δ 4.02 (3H, s), 7.27 (1H, dd, J=9.0, 0.8 Hz), 8.17 (1H, dd, J=9.0, 7.5 Hz), 10.24 (1H, d, J=1.5 Hz).

B) 3-(azidomethyl)-2-fluoro-4-methoxybenzonitrile

To a mixture of 2-fluoro-3-formyl-4-methoxybenzonitrile (5.02 g), ethanol (30 ml) and THF (30 ml) was added sodium tetrahydroborate (0.318 g) at 0° C., and the mixture was stirred at the same temperature for 20 min. The reaction was discontinued by adding saturated aqueous ammonium chloride solution and the mixture was extracted with ethyl acetate. The organic layer was washed with saturated brine, dried over anhydrous sodium sulfate, filtered, and concentrated under reduced pressure to give 2-fluoro-3-(hydroxymethyl)-4-methoxybenzonitrile (4.63 g) as a crude product. To a mixture of the thus-obtained 2-fluoro-3-(hydroxymethyl)-4-methoxybenzonitrile (4.63 g) and THF (50 ml) were added DPPA (6.59 mL) and DBU (5.78 mL) at 0° C., and the mixture was stirred at room temperature for 5 hr. The mixture was concentrated under reduced pressure, and the residue was purified by silica gel column chromatography (ethyl acetate/hexane) to give the title compound (5.27 g).

$^1$H NMR (300 MHz, DMSO-$d_6$) δ 3.97 (3H, s), 4.46 (2H, d, J=1.9 Hz), 7.18 (1H, d, J=8.7 Hz), 7.98 (1H, dd, J=8.7, 7.9 Hz).

C) tert-butyl [(3-cyano-2-fluoro-6-methoxyphenyl) methyl]Carbamate

To a mixture of 3-(azidomethyl)-2-fluoro-4-methoxybenzonitrile (5.51 g), THF (60 ml) and water (3 ml) was added triphenylphosphine (7.71 g). The mixture was stirred at room temperature for 18 hr, $Boc_2O$ (6.83 mL) was added, and the mixture was stirred at room temperature for 30 min. The mixture was concentrated under reduced pressure, and the residue was purified by silica gel column chromatography (ethyl acetate/hexane) to give the title compound (6.88 g).

$^1$H NMR (300 MHz, DMSO-$d_6$) δ 1.36 (9H, s), 3.90 (3H, s), 4.14 (2H, br d, J=4.9 Hz), 6.99-7.11 (2H, m), 7.84 (1H, dd, J=8.7, 7.5 Hz).

D) 3-(aminomethyl)-2-fluoro-4-methoxybenzonitrile Hydrochloride

To a mixture of tert-butyl [(3-cyano-2-fluoro-6-methoxyphenyl)methyl]carbamate (6.88 g) and ethyl acetate (50 ml) was added 4 M hydrogen chloride/ethyl acetate (150 ml). The mixture was stirred at room temperature for 1.5 hr, and the precipitated solid was filtered, washed with ethyl acetate, and dried to give the title compound (4.58 g).

$^1$H NMR (300 MHz, DMSO-$d_6$) δ 3.97 (3H, s), 4.01 (2H, d, J=1.5 Hz), 7.17 (1H, d, J=8.3 Hz), 7.95-8.20 (4H, m).

E) N-[(3-cyano-2-fluoro-6-methoxyphenyl)methyl]-6-(difluoromethoxy)-5-fluoropyridine-3-carboxamide A mixture of 6-(difluoromethoxy)-5-fluoronicotinic acid (1.05 g), 3-(aminomethyl)-2-fluoro-4-methoxybenzonitrile hydrochloride (1.05 g), WSC·HCl (1.21 g), HOBt (0.851 g), DIPEA (2.54 ml) and DMF (10 ml) was stirred at room temperature for 18 hr. Water was added to the reaction mixture, and the precipitated solid was collected by filtration and dried to give the title compound (1.58 g).

$^1$H NMR (300 MHz, DMSO-$d_6$) δ3.93 (3H, s), 4.49 (2H, d, J=4.1 Hz), 7.10 (1H, d, J=8.7 Hz), 7.78 (1H, t, J=72.0 Hz), 7.89 (1H, dd, J=8.7, 7.9 Hz), 8.27 (1H, dd, J=10.7, 2.1 Hz), 8.52 (1H, d, J=1.9 Hz), 8.88 (1H, t, J=4.9 Hz).

The Example compounds are shown in the following Tables. In the Tables, MS means Found. The compounds of Examples 2-6, 8, 10, 11, 13-15, 18-30 in the following Tables were produced according to the methods shown in the above-mentioned Examples or a method analogous thereto.

| Example No. | IUPAC name | structural formula | salt | MS |
|---|---|---|---|---|
| [Table 1-1] | | | | |
| 1 | N-[(2-bromo-5-cyanophenyl)methyl]-3-fluoro-4-(trifluoromethoxy)-benzamide | 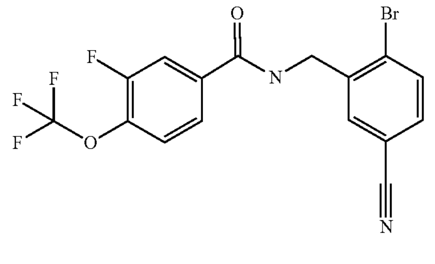 | | 414.6 |
| 2 | N-[(2-bromo-5-cyanophenyl)methyl]-6-(difluoromethoxy)-5-fluoropyridine-3-carboxamide | 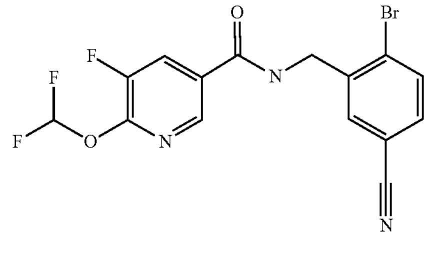 | | 398.1 |

-continued

| Example No. | IUPAC name | structural formula | salt | MS |
|---|---|---|---|---|
| 3 | N-[(2-bromo-5-cyanophenyl)methyl]-4-(difluoromethoxy)-3-fluorobenzamide | 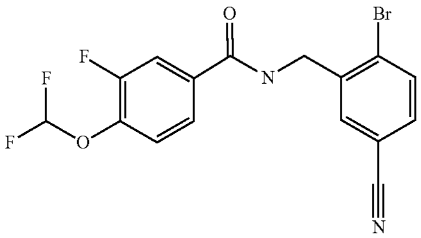 | | 397.0 |
| 4 | N-[(5-cyano-2-cyclopropylphenyl)-methyl]-3-fluoro-4 (trifluoromethoxy)-benzamide | 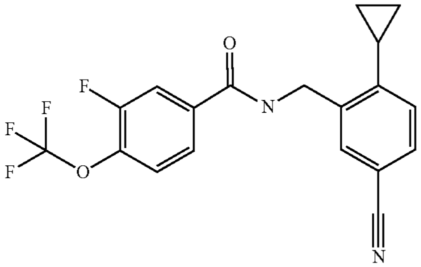 | | 377.1 |
| 5 | N-[(5-cyano-2-cyclopropylphenyl)-methyl]-6-(difluoromethoxy)-5-fluoropyridine-3-carboxamide | 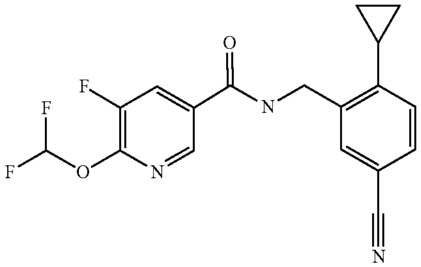 | | 360.3 |

[Table 1-2]

| | | | | |
|---|---|---|---|---|
| 6 | N-[(5-cyano-2-cyclopropylphenyl)-methyl]-4-(difluoromethoxy)-3-fluorobenzamide | 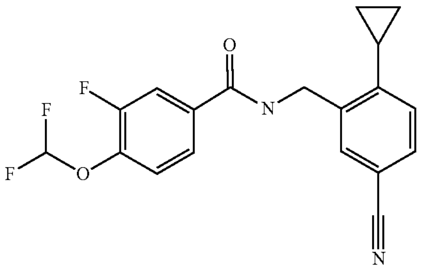 | | 358.8 |
| 7 | N-[(5-cyano-2-methoxyphenyl)-methyl]-6-(difluoromethoxy)-5-fluoropyridine-3-carboxamide | 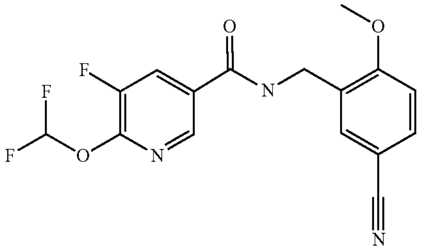 | | 349.9 |

-continued

| Example No. | IUPAC name | structural formula | salt | MS |
|---|---|---|---|---|
| 8 | N-[(5-cyano-2-methylphenyl)-methyl]-6-(difluoromethoxy)-5-fluoropyridine-3-carboxamide | 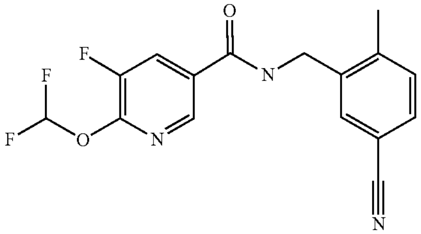 | | 334.0 |
| 9 | N-[(5-cyano-2-methoxypyridin-3-yl)methyl]-6-(difluoromethoxy)-fluoropyridine-3-carboxamide | 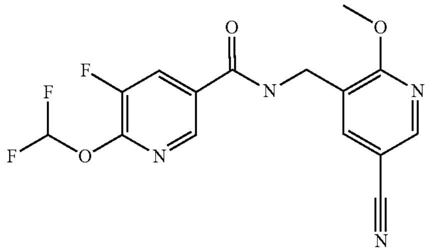 | | 350.9 |
| 10 | N-[(5-cyano-2-methoxyphenyl)-methyl]-4-(difluoromethoxy)-3-fluorobenzamide | 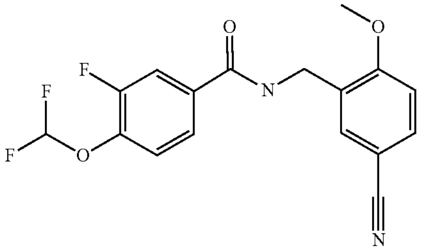 | | 349.1 |

[Table 1-3]

| | | | | |
|---|---|---|---|---|
| 11 | N-[(5-cyano-2-methoxyphenyl)-methyl]-3-fluoro-4-(trifluoromethoxy)-benzamide | 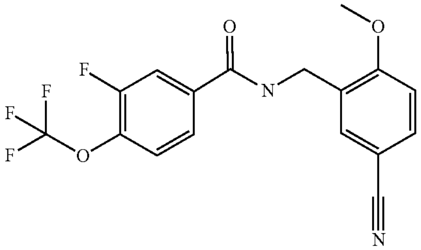 | | 367.1 |
| 12 | N-[(5-cyano-2-fluorophenyl)-methyl]-6-(difluoromethoxy)-5-fluoropyridine-3-carboxamide | 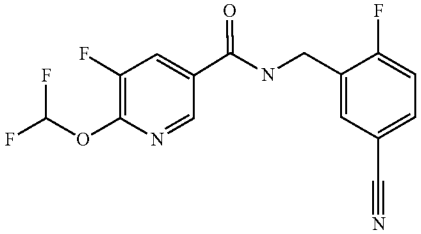 | | 338.0 |
| 13 | N-{[5-cyano-2-(2,2,2-trifluoroethoxy)-phenyl]-methyl}-6-(difluoromethoxy)-5-fluoropyridine-3-carboxamide | 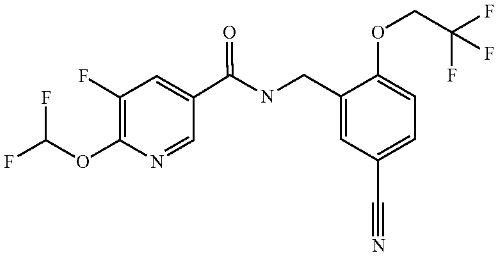 | | 418.0 |

-continued

| Example No. | IUPAC name | structural formula | salt | MS |
|---|---|---|---|---|
| 14 | N-{[5-cyano-2-(2,2-difluoroethoxy)-phenyl]-methyl}-6-(difluoromethoxy)-5-fluoropyridine-3-carboxamide | 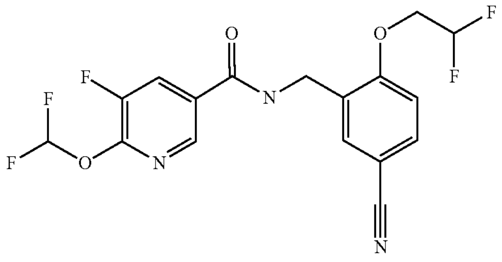 | | 400.1 |
| 15 | N-[(3-cyano-6-fluoro-2-methoxyphenyl)-methyl]-(difluoromethoxy)-5-fluoropyridine-3-carboxamide | 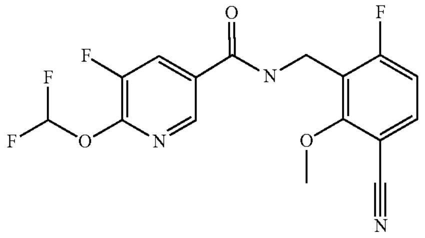 | | 368.0 |

[Table 1-4]

| Example No. | IUPAC name | structural formula | salt | MS |
|---|---|---|---|---|
| 16 | N-[(5-cyano-2-methoxypyridin-3-yl)methyl]-5-(trifluoromethyl)-thiophene-2-carboxamide | 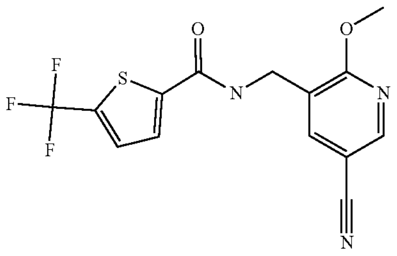 | | 340.1 |
| 17 | N-[(3-cyano-2-fluoro-6-methoxyphenyl)-methyl]-6-(difluoromethoxy)-5-fluoropyridine-3-carboxamide | 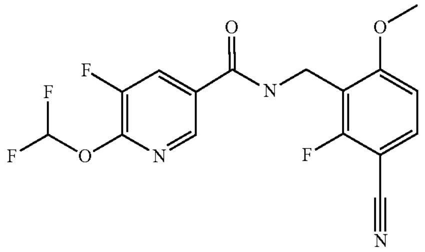 | | 368.0 |
| 18 | N-[(3-cyano-6-fluoro-2-methylphenyl)-methyl]-6-(difluoromethoxy)-5-fluoropyridine-3-carboxamide | 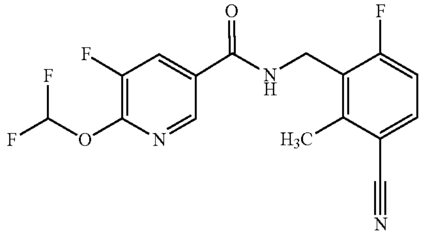 [SMILES: Cc1c(C#N)ccc(F)c1CNC(=O)c1cnc(OC(F)F)c(F)c1] | | 352.1 |

-continued

| Example No. | IUPAC name | structural formula | salt | MS |
|---|---|---|---|---|
| 19 | N-[(6-cyano-3-methoxypyridin-2-yl)methyl]-6-(difluoromethoxy)-5-fluoropyridine-3-carboxamide | 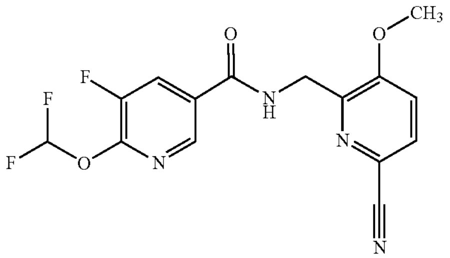 [SMILES: COc1ccc(C#N)nc1CNC(=O)c1cnc(OC(F)F)c(F)c1] | | 351.2 |
| 20 | N-[(5-cyano-3-fluoro-2-methoxyphenyl)-methyl]-6-(difluoromethoxy)-5-fluoropyridine-3-carboxamide | 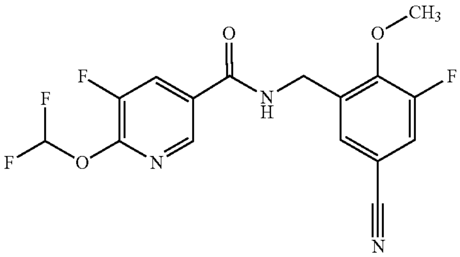 [SMILES: COc1c(F)cc(C#N)cc1CNC(=O)c1cnc(OC(F)F)c(F)c1] | | 368.1 |

[Table 1-5]

| | | | | |
|---|---|---|---|---|
| 21 | N-[(5-cyano-3-fluoro-2-methoxyphenyl)-methyl]-5-fluoro-6-methoxypyridine-3-carboxamide | 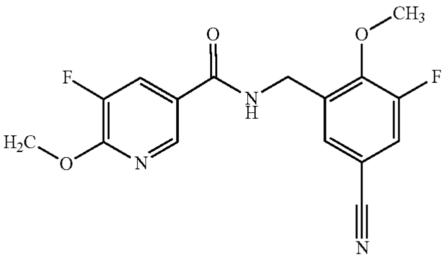 [SMILES: COc1ncc(C(=O)NCc2cc(C#N)cc(F)c2OC)cc1F] | | 332.1 |
| 22 | N-[(2-cyano-3-fluoro-5-methoxypyridin-4-yl)methyl]-6-(difluoromethoxy)-5-fluoropyridine-3-carboxamide | 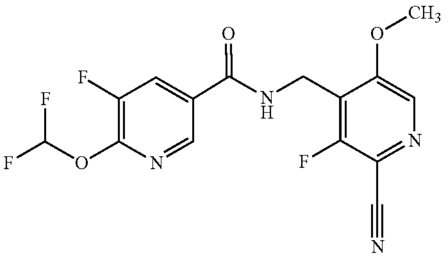 [SMILES: COc1cnc(C#N)c(F)c1CNC(=O)c1cnc(OC(F)F)c(F)c1] | | 369.1 |
| 23 | N-[(5-cyano-4-fluoro-2-methoxyphenyl)-methyl]-6-(difluoromethoxy)-5-fluoropyridine-3-carboxamide | 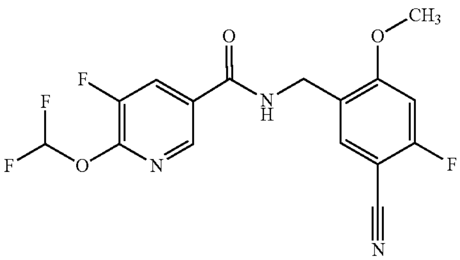 [SMILES: COc1cc(F)c(C#N)cc1CNC(=O)c1cnc(OC(F)F)c(F)c1] | | 368.1 |

-continued

| Example No. | IUPAC name | structural formula | salt | MS |
|---|---|---|---|---|
| 24 | N-[(3-cyano-5-methoxyphenyl)-methyl]-6-(difluoromethoxy)-5-fluoropyridine-3-carboxamide | 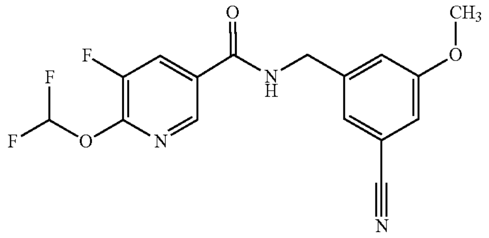 [SMILES: COc1cc(C#N)cc(CNC(=O)c2cnc(OC(F)F)c(F)c2)c1] | | 350.1 |
| 25 | N-[(5-cyano-2-fluoro-3-methoxyphenyl)-methyl]-6-(difluoromethoxy)-5-fluoropyridine-3-carboxamide | 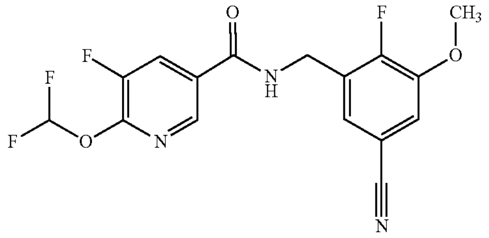 [SMILES: COc1cc(C#N)cc(CNC(=O)c2cnc(OC(F)F)c(F)c2)c1F] | | 368.1 |

[Table 1-6]

| Example No. | IUPAC name | structural formula | salt | MS |
|---|---|---|---|---|
| 26 | N-[(5-cyano-2-fluoro-3-methoxyphenyl)-methyl]-5-fluoro-6-methoxypyridine-3-carboxamide | 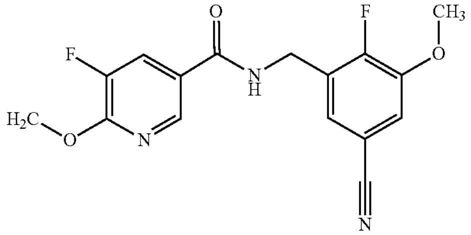 | | 332.1 |
| 27 | N-[(6-cyano-3-methoxy-2-methyl-pyridin-4-yl)methyl]-6-(difluoromethoxy)-5-fluoropyridine-3-carboxamide | 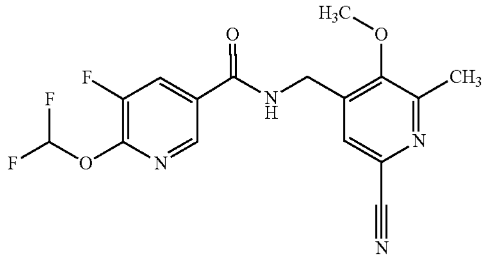 [SMILES: COc1c(CNC(=O)c2cnc(OC(F)F)c(F)c2)cc(C#N)nc1C] | | 365.1 |
| 28 | N-[(2-cyano-5-methoxypyridin-4-yl)methyl]-6-(difluoromethoxy)-5-fluoropyridine-3-carboxamide | 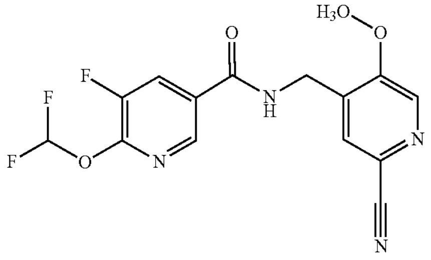 [SMILES: N#Cc1cc(CNC(=O)c2cnc(OC(F)F)c(F)c2)c(OO)cn1] | | 351.1 |
| 29 | N-[(2-cyano-5-methoxypyridin-4-yl)methyl]-4-(trifluoromethoxy)-bezamide | 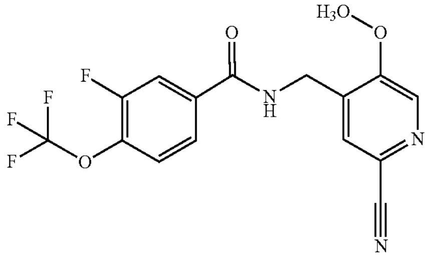 [SMILES: N#Cc1cc(CNC(=O)c2ccc(OC(F)(F)F)c(F)c2)c(OO)cn1] | | 350.1 |

-continued

| Example No. | IUPAC name | structural formula | salt | MS |
|---|---|---|---|---|
| 30 | N-[(2-cyano-5-methoxypyridin-4-yl)methyl]-3-fluoro-4-(trifluoromethyl)-bezamide | 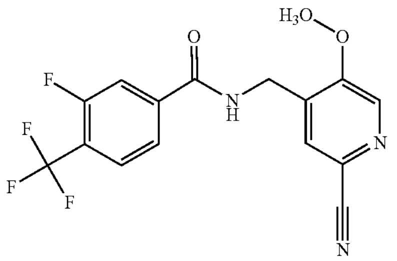 [SMILES: N#Cc1cc(CNC(=O)c2ccc(C(F)(F)F)c(F)c2)c(OO)cn1] | | 352.1 |

Experimental Example 1

NR2B $Ca^{2+}$ Influx Assay

To confirm the "antagonistic action on an NMDA receptor containing the NR2B subunit" of the compound of the present invention, human embryonic kidney cell expressing the "NMDA receptor composed of four subunits including 2 sets of heterodimers of NR1 and NR2B", specifically HEK293 cell expressing human glutamate ionotropic receptor NMDA type subunit 1 (GRIN1) and human glutamate ionotropic receptor NMDA type subunit 2B (GRIN2B), was used and the activation suppressive effect on the receptors was measured.

HEK293 cells that express GRIN1 and GRIN2B were purchased from ChanTest (Human NMDA (NR1/NR2B) Receptor-expressing, stable replicating cell line (HEK293) catalog No. CT6121).

As an index of the NMDA receptor activation, intracellular calcium ion ($Ca^2$+) influx caused by the binding of glycine and glutamic acid with NR1 and NR2B, respectively, was used.

HEK293 cells that express GRIN1 and GRIN2B were cultured in DMEM/F-12 (COSMO BIO, 10-092-CM) medium added with 10% FBS (fetal bovine serum, AusGene), 100 units/mL penicillin, 100 μg/mL streptomycin, 500 μg/mL neomycin, 100 μg/mL Zeocin (registered trade mark, Invitrogen), 5 μg/mL Blasticidin in a cell culture flask in an incubator (under 37° C., 5% $CO_2$).

The cells were detached from the flask with trypsin the day before the assay, suspended in a seeding medium (DMEM (Invitrogen, 31053) added with 10% FBS, 100 units/mL penicillin, 100 μg/mL streptomycin) at $8\times10^5$ cells/mL, seeded by 25 μL per well in a 384-well plate (Falcon, 356663) at 20000 cells/well, and cultured overnight in an incubator. On the day of the assay, tetracycline (Wako Pure Chemical Industries, Ltd., 209-16561) was diluted with the seeding medium at 2 μg/mL, added at 25 μL/well to the plate seeded with the cells, and cultured for 2 hr in an incubator. Thereafter, the medium was removed, and the cells were washed with 50 μL/well assay buffer (137 mM NaCl, 4 mM KCl, 1.8 mM $CaCl_2$, 10 mM HEPES (pH 7.2), 10 mM Glucose, 0.1% BSA). Then, a loading buffer (assay buffer added with 2.5 μM Fluo-4AM, 2 mM Amaranth, 1 mM Tartrazine) was added at 25 μL/well, and the cells were incubated in the incubator for 30 min, and at room temperature for 15 min. A solution of the Example compound diluted with the above-mentioned assay buffer at 30 μM (final concentration 10 μM) was added at 25 μL/well, and the cells were left standing for 15 min at room temperature. Using FDSS7000EX/μCELL (Hamamatsu Photonics K.K.), an assay buffer containing 30 μM glutamic acid and 30 μM glycine was added at 25 μL/well, and fluorescence signals with wavelengths of Excitation 480 nm and Emission 540 nm were measured every 3 seconds for 5 min. The inhibitory activity was calculated as a relative activity value (inhibitory rate) that inhibits 100% of the cumulative value of the fluorescence value of a well added with an assay buffer free of glutamic acid, glycine, relative to the cumulative value of the fluorescence value of each well. The results are shown in Table 2.

TABLE 2

| Example No. | inhibitory rate (10 μM compound concentration) |
|---|---|
| 1 | 86 |
| 2 | 92 |
| 3 | 93 |
| 4 | 94 |
| 5 | 95 |
| 6 | 93 |
| 7 | 94 |
| 8 | 83 |
| 9 | 94 |
| 10 | 95 |
| 11 | 96 |
| 12 | 91 |
| 13 | 93 |
| 14 | 92 |
| 15 | 89 |
| 16 | 94 |
| 17 | 96 |
| 18 | 66 |
| 19 | 89 |
| 20 | 97 |
| 21 | 94 |
| 22 | 94 |
| 23 | 98 |
| 24 | 97 |
| 25 | 89 |
| 26 | 75 |
| 27 | 77 |
| 28 | 91 |
| 29 | 92 |
| 30 | 87 |

As shown in the above-mentioned Table 2, the compound of the present invention suppressed intracellular calcium ion ($Ca^{2+}$) influx in the NMDA receptors containing the NR2B subunit. That is, it has been confirmed that the compound of the present invention has an antagonistic action on an NMDA receptor containing the NR2B subunit.

Experimental Example 2

In Vivo [$^3$H]MK-801 Binding Test

To confirm the "functionally antagonistic action in vivo for NMDA receptor containing NR2B subunit" that the compound of the present invention has, a binding test was performed using a tritium-labeled form of MK-801 ((5R, 10S)-5-methyl-10,11-dihydro-5H-5,10-epiminodibenzo[a, d][7]annulene) ([$^3$H]MK-801) which is a compound that binds to the gate of the NMDA receptor.

An Example compound (1 mg/kg/2 mL, 0.5% MC water) or vehicle (kg/2 mL, 0.5% MC water) was orally administered (p.o.) to Sprague Dawley rats (body weight 180-260 g). After a certain period of time (near the time when the maximum blood concentration was reached), [$^3$H]MK-801 (20 μCi/kg/mL, Muromachi Kikai Co., Ltd.) was intravenously administered from the tail vein. After 10 min, the rats were euthanized by decapitation, the head was opened, and the hippocampus was collected. To the collected hippocampus was added 30 times the tissue weight (30 mL per 1 g of tissue) of ice-cooled 20 mM Hepes (pH 7.5, Hampton Research), and the mixture was homogenized by a homogenizer (MICROTEC CO., LTD.) for 10 seconds. 600 μL of the homogenate was added to a manifold filtration system (Millipore) set with a GF/B Watman glass filter (GE Healthcare) that was previously treated with 0.5% polyethyleneimine (Fujifilm Wako Pure Chemical Corporation), and suction filtered. The filter was washed 4 times with 5 mL of ice-cooled physiological saline (Otsuka Pharmaceutical Co., Ltd.) and placed in a scintillation vial. 10 mL of liquid scintillator A (Fujifilm Wako Pure Chemical Corporation) was added, and the residual radioactivity was measured by a liquid scintillation counter (ALOKA LSC-6100). The residual radioactivity of 100 μL of the homogenate before filtration through the glass filter was also measured in the same manner. By calculating [residual radioactivity in filter/residual radioactivity in 100 μL of homogenate], correction by the dose of [$^3$H]MK-801 was performed, and the value was used as a binding ratio of [$^3$H]MK-801 in the NMDA receptor expressed in the hippocampus tissue of each individual. Then, the binding ratio of [$^3$H]MK-801 in the Vehicle administration group was taken as 100%, and the binding ratio of [$^3$H]MK-801 in the group subcutaneously administered with an excess amount of MK-801 maleate (2 mg/kg/2 mL, 0.5% MC water) was taken as 0%. The difference between the binding rate of [$^3$H]MK-801 in the group orally administered with the Example compound and the vehicle group (100%) was taken as the [$^3$H]MK-801 binding inhibitory rate by the Example compound, and data analysis was performed. The results are shown in Table 3.

TABLE 3

| Example No. | inhibitory rate (1 mg/kg, p.o.) |
|---|---|
| 9 | 10% |
| 17 | 17% |

Formulation Example 1 (Production of Capsule)

| | | |
|---|---|---|
| 1) compound of Example 1 | | 30 mg |
| 2) finely-powdered cellulose | | 10 mg |
| 3) lactose | | 19 mg |
| 4) magnesium stearate | | 1 mg |
| | total | 60 mg |

1), 2), 3) and 4) are mixed and filled in a gelatin capsule.

Formulation Example 2 (Production of Tablets)

| | | |
|---|---|---|
| 1) compound of Example 1 | | 30 g |
| 2) lactose | | 50 g |
| 3) cornstarch | | 15 g |
| 4) calcium carboxymethylcellulose | | 44 g |
| 5) magnesium stearate | | 1 g |
| 1000 tablets | total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

INDUSTRIAL APPLICABILITY

The compound of the present invention can have an antagonistic action on an NMDA receptor containing the NR2B subunit, and is expected to be useful as a prophylactic or therapeutic agent for depression, bipolar disorder, migraine, pain, peripheral symptoms of dementia and the like.

This application is a national stage filing under 35 U.S.C. § 371 of International Application No. PCT/JP2020/002216, filed Jan. 24, 2019, which claims the benefit of priority of Japanese Patent Application No. 2019-010536, filed Jan. 24, 2019, the contents of each of which are incorporated by reference herein in their entireties.

The invention claimed is:

1. A compound represented by the formula (I):

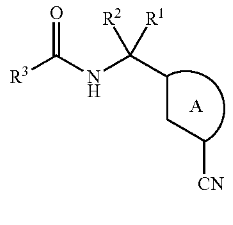

(I)

wherein ring A is a 6-membered aromatic ring substituted by a —CN group and a

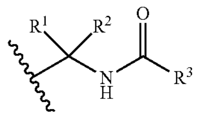

group, wherein the —CN group is meta relative to the

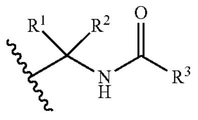

group;

ring A is further substituted by 1 to 4 substituents selected from (1) a $C_{1-3}$ alkyl group, (2) a $C_{1-3}$ haloalkyl group, (3) an optionally substituted cyclic group, (4) an optionally substituted $C_{1-6}$ alkoxy group, and (5) a halogen atom;

$R^1$ and $R^2$ are each independently a hydrogen atom or a $C_{1-3}$ alkyl group optionally substituted by fluorine atom(s);

$R^3$ is (1) a group represented by

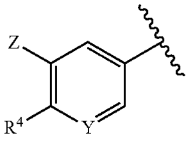

wherein $R^4$ is a substituent selected from (1) a $C_{1-3}$ haloalkyl group, (2) an optionally substituted $C_{3-7}$ cycloalkyl group, and (3) an optionally substituted $C_{1-6}$ alkoxy group, Y is a nitrogen atom or $CR^6$, $R^6$ is a hydrogen atom or a halogen atom, and Z is a hydrogen atom or a halogen atom, or (2) a group represented by

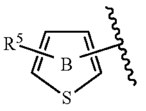

wherein $R^5$ is a substituent selected from (1) a $C_{1-3}$ haloalkyl group, (2) an optionally substituted $C_{3-7}$ cycloalkyl group, and (3) an optionally substituted $C_{1-6}$ alkoxy group, and ring B is a thiophene ring optionally further substituted by one halogen atom, or a salt thereof.

2. The compound according to claim 1, wherein ring A is a 6-membered aromatic ring further substituted by 1 or 2 substituents selected from (1) a $C_{1-3}$ alkyl group, (2) a $C_{3-10}$ cycloalkyl group, (3) a $C_{1-6}$ alkoxy group optionally substituted by 1 to 3 halogen atoms, and (4) a halogen atom;

$R^1$ and $R^2$ are each a hydrogen atom;

$R^3$ is (1) a group represented by

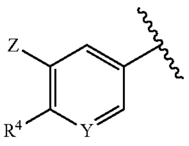

wherein $R^4$ is a $C_{1-3}$ haloalkyl group or a $C_{1-6}$ alkoxy group optionally substituted by 1 to 3 halogen atoms, Y is a nitrogen atom or $CR^6$, $R^6$ is a hydrogen atom, Z is a halogen atom or a hydrogen atom; or (2) a group represented by

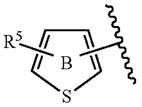

wherein $R^5$ is a $C_{1-3}$ haloalkyl group, and ring B is a thiophene ring optionally further substituted by one halogen atom;

or a salt thereof.

3. N-[(5-cyano-2-methoxypyridin-3-yl)methyl]-6-(difluoromethoxy)-5-fluoropyridine-3-carboxamide or a salt thereof.

4. N-[(3-cyano-2-fluoro-6-methoxyphenyl)methyl]-6-(difluoromethoxy)-5-fluoropyridine-3-carboxamide or a salt thereof.

5. A medicament comprising the compound according to claim 1 or a salt thereof.

6. The compound according to claim 1 or a salt thereof, wherein:

$R^1$ and $R^2$ are each a hydrogen atom.

7. The compound according to claim 1 or a salt thereof, wherein:

$R^3$ is a group represented by:

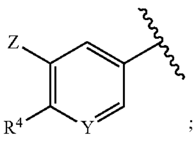

;

$R^4$ is a $C_{1-6}$ alkoxy group optionally substituted by 1 to 3 halogen atoms;

Y is a nitrogen atom; and

Z is a halogen atom.

8. The compound according to claim 1 or a salt thereof, wherein:

$R^3$ is a group represented by:

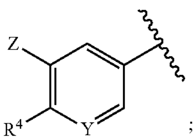

;

$R^4$ is a $C_{1-3}$ haloalkyl group or a $C_{1-6}$ alkoxy group optionally substituted by 1 to 3 halogen atoms;

Y is $CR^6$; and one of $R^6$ and Z is a halogen atom and the other is a hydrogen atom.

9. The compound according to claim 1 or a salt thereof, wherein:

ring A is a 6-membered aromatic ring further substituted by 1 or 2 substituents selected from (1) a $C_{1-3}$ alkyl group, (2) a $C_{3-10}$ cycloalkyl group, (3) a $C_{1-6}$ alkoxy group optionally substituted by 1 to 3 halogen atoms, and (4) a halogen atom;

$R^1$ and $R^2$ are each a hydrogen atom;

$R^3$ is a group represented by:

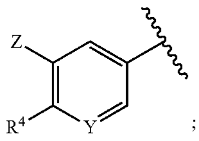

;

$R^4$ is a $C_{1-6}$ alkoxy group optionally substituted by 1 to 3 halogen atoms;

Y is a nitrogen atom; and

Z is a halogen atom.

10. The compound according to claim 9 or a salt thereof, wherein:

ring A is a benzene ring or pyridine ring, further substituted by 1 or 2 substituents selected from (1) methyl, (2) cyclopropyl, (3) methoxy or ethoxy, optionally substituted by 1 to 3 fluorine atoms, and (4) a fluorine atom or bromine atom;

$R^1$ and $R^2$ are each a hydrogen atom;

$R^3$ is a group represented by:

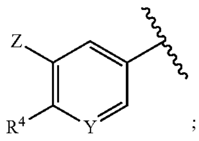

;

$R^4$ is methoxy optionally substituted by 1 to 3 fluorine atoms;

Y is a nitrogen atom; and

Z is a fluorine atom.

11. The compound according to claim 1 or a salt thereof, wherein:

ring A is a 6-membered aromatic ring further substituted by 1 or 2 substituents selected from (1) a $C_{1-3}$ alkyl group, (2) a $C_{3-10}$ cycloalkyl group, (3) a $C_{1-6}$ alkoxy group optionally substituted by 1 to 3 halogen atoms, and (4) a halogen atom;

$R^1$ and $R^2$ are each a hydrogen atom;

$R^3$ is a group represented by:

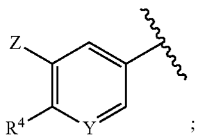

;

$R^4$ is a $C_{1-3}$ haloalkyl group or a $C_{1-6}$ alkoxy group optionally substituted by 1 to 3 halogen atoms;

Y is $CR^6$;

$R^6$ is a hydrogen atom; and

Z is a hydrogen atom or a halogen atom.

12. The compound according to claim 11 or a salt thereof, wherein:

ring A is a benzene ring or pyridine ring, further substituted by 1 or 2 substituents selected from (1) methyl, (2) cyclopropyl, (3) methoxy or ethoxy, optionally substituted by 1 to 3 fluorine atoms, and (4) a fluorine atom or bromine atom;

$R^1$ and $R^2$ are each a hydrogen atom;

$R^3$ is a group represented by:

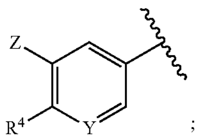

;

$R^4$ is trifluoromethyl or methoxy optionally substituted by 1 to 3 fluorine atoms;

Y is $CR^6$;

$R^6$ is a hydrogen atom; and

Z is a hydrogen atom or a fluorine atom.

13. The compound according to claim 1 or a salt thereof, wherein:

ring A is a benzene ring or a pyridine ring, further substituted by 1 or 2 substituents selected from methoxy and a fluorine atom;

$R^1$ and $R^2$ are each a hydrogen atom;

$R^3$ is a group represented by:

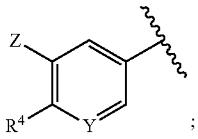

;

$R^4$ is methoxy optionally substituted by 1 to 3 fluorine atoms;

Y is a nitrogen atom; and

Z is a fluorine atom.

14. The compound according to claim 1 or a salt thereof, wherein the compound is selected from N-[(2-bromo-5-cyanophenyl)methyl]-3-fluoro-4-(trifluoromethoxy)benzamide, N-[(2-bromo-5-cyanophenyl)methyl]-6-(difluoromethoxy)-5-fluoropyridine-3-carboxamide, N-[(2-bromo-5-cyanophenyl)methyl]-4-(difluoromethoxy)-3-fluorobenzamide, N-[(5-cyano-2-cyclopropylphenyl)methyl]-3-fluoro-4-(trifluoromethoxy)benzamide, N-[(5-cyano-2-cyclopropylphenyl)methyl]-6-(difluoromethoxy)-5-fluoropyridine-3-carboxamide,
N-[(5-cyano-2-cyclopropylphenyl)methyl]-4-(difluoromethoxy)-3-fluorobenzamide,
N-[(5-cyano-2-methoxyphenyl)methyl]-6-(difluoromethoxy)-5-fluoropyridine-3-carboxamide,
N-[(5-cyano-2-methylphenyl)methyl]-6-(difluoromethoxy)-5-fluoropyridine-3-carboxamide,
N-[(5-cyano-2-methoxypyridin-3-yl)methyl]-6-(difluoromethoxy)-5-fluoropyridine-3-carboxamide,
N-[(5-cyano-2-methoxyphenyl)methyl]-4-(difluoromethoxy)-3-fluorobenzamide,
N-[(5-cyano-2-methoxyphenyl)methyl]-3-fluoro-4-(trifluoromethoxy)benzamide,
N-[(5-cyano-2-fluorophenyl)methyl]-6-(difluoromethoxy)-5-fluoropyridine-3-carboxamide,
N-{[5-cyano-2-(2,2,2-trifluoroethoxy)phenyl]methyl}-6-(difluoromethoxy)-5-fluoropyridine-3-carboxamide,
N-{[5-cyano-2-(2,2-difluoroethoxy)phenyl]methyl}-6-(difluoromethoxy)-5-fluoropyridine-3-carboxamide,
N-[(3-cyano-6-fluoro-2-methoxyphenyl)methyl]-6-(difluoromethoxy)-5-fluoropyridine-3-carboxamide,
N-[(5-cyano-2-methoxypyridin-3-yl)methyl]-5-(trifluoromethyl)thiophene-2-carboxamide,
N-[(3-cyano-2-fluoro-6-methoxyphenyl)methyl]-6-(difluoromethoxy)-5-fluoropyridine-3-carboxamide,
N-[(3-cyano-6-fluoro-2-methylphenyl)methyl]-6-(difluoromethoxy)-5-fluoropyridine-3-carboxamide,
N-[(6-cyano-3-methoxypyridin-2-yl)methyl]-6-(difluoromethoxy)-5-fluoropyridine-3-carboxamide,
N-[(5-cyano-3-fluoro-2-methoxyphenyl)methyl]-6-(difluoromethoxy)-5-fluoropyridine-3-carboxamide,
N-[(5-cyano-3-fluoro-2-methoxyphenyl)-methyl]-5-fluoro-6-methoxypyridine-3-carboxamide,
N-[(2-cyano-3-fluoro-5-methoxypyridin-4-yl)methyl]-6-(difluoromethoxy)-5-fluoropyridine-3-carboxamide,
N-[(5-cyano-4-fluoro-2-methoxyphenyl)-methyl]-6-(difluoromethoxy)-5-fluoropyridine-3-carboxamide,
N-[(3-cyano-5-methoxyphenyl)-methyl]-6-(difluoromethoxy)-5-fluoropyridine-3-carboxamide,
N-[(5-cyano-2-fluoro-3-methoxyphenyl)-methyl]-6-(difluoromethoxy)-5-fluoropyridine-3-carboxamide,
N-[(5-cyano-2-fluoro-3-methoxyphenyl)-methyl]-5-fluoro-6-methoxypyridine-3-carboxamide,
N-[(6-cyano-3-methoxy-2-methylpyridin-4-yl)methyl]-6-(difluoromethoxy)-5-fluoropyridine-3-carboxamide,
N-[(2-cyano-5-methoxypyridin-4-yl)methyl]-6-(difluoromethoxy)-5-fluoropyridine-3-carboxamide,
N-[(2-cyano-5-methoxypyridin-4-yl)methyl]-4-(trifluoromethoxy)bezamide, and
N-[(2-cyano-5-methoxypyridin-4-yl)methyl]-3-fluoro-4-(trifluoromethyl)bezamide.

15. A method for antagonizing an NMDA receptor containing an NR2B subunit in a mammal, comprising administering an effective amount of the compound according to claim 1 or a salt thereof to the mammal.

16. A method for treating depression, bipolar disorder, migraine, pain, or peripheral symptoms of dementia in a mammal, comprising administering an effective amount of the compound according to claim 1 or a salt thereof to the mammal.

* * * * *